(12) United States Patent
Tsurumoto et al.

(10) Patent No.: US 12,342,773 B2
(45) Date of Patent: Jul. 1, 2025

(54) METHOD OF TREATING PLANT, METHOD OF PRODUCING PLANT INFECTED WITH MICROORGANISM, METHOD OF PRODUCING FERMENTED PLANT PRODUCT, AND PLANT TREATMENT APPARATUS

(71) Applicant: NICHIA CORPORATION, Anan (JP)

(72) Inventors: Tomohiro Tsurumoto, Yokohama (JP); Yasuo Fujikawa, Yokohama (JP); Yushi Onoda, Tokushima (JP)

(73) Assignee: NICHIA CORPORATION, Anan (JP)

( * ) Notice: Subject to any disclaimer, the term of this patent is extended or adjusted under 35 U.S.C. 154(b) by 0 days.

(21) Appl. No.: 18/496,031

(22) Filed: Oct. 27, 2023

(65) Prior Publication Data
US 2024/0138329 A1  May 2, 2024

(30) Foreign Application Priority Data

Oct. 28, 2022 (JP) .................................. 2022-173633

(51) Int. Cl.
*A01H 3/02* (2006.01)
*A01G 7/04* (2006.01)

(52) U.S. Cl.
CPC ............... *A01H 3/02* (2013.01); *A01G 7/045* (2013.01)

(58) Field of Classification Search
CPC .......... A01H 3/02; A01G 7/045; A01G 9/247; A01G 7/06; A01G 9/249
See application file for complete search history.

(56) References Cited

U.S. PATENT DOCUMENTS

| | | | |
|---|---|---|---|
| 2020/0120886 A1* | 4/2020 | Geltner | A01G 7/04 |
| 2020/0359573 A1* | 11/2020 | Yost | A01G 7/04 |
| 2021/0112726 A1* | 4/2021 | Okazawa | A01G 22/15 |
| 2021/0123043 A1* | 4/2021 | Wigley | A01N 63/00 |
| 2021/0400892 A1* | 12/2021 | Rouxel | A01G 9/023 |
| 2022/0313765 A1* | 10/2022 | Tsurumoto | A61K 36/185 |
| 2023/0329163 A1* | 10/2023 | Massey | A01G 7/045 |
| 2024/0138329 A1* | 5/2024 | Tsurumoto | A01G 7/06 |

FOREIGN PATENT DOCUMENTS

| | | | | |
|---|---|---|---|---|
| EP | 3834605 A2 | 6/2021 | | |
| EP | 3997976 A1 | 5/2022 | | |
| JP | H11106 A | 1/1999 | | |
| JP | 2016007185 A | 1/2016 | | |
| JP | 2018186802 A | 11/2018 | | |
| JP | 2020039352 A | 3/2020 | | |
| JP | 2020525002 A | 8/2020 | | |
| WO | 2015137825 A1 | 9/2015 | | |
| WO | 2019002946 A1 | 1/2019 | | |
| WO | WO-2019203597 A8 * | 11/2019 | ............. | A01G 7/045 |
| WO | 2020095117 A2 | 5/2020 | | |

* cited by examiner

*Primary Examiner* — David A Vanore
(74) *Attorney, Agent, or Firm* — Hunton Andrews Kurth LLP

(57) ABSTRACT

A method of treating a plant by irradiating the plant with light in a wavelength range of 300 nm to 325 nm at a fluence of 4,000 μmol/m² to 50,000 μmol/m², while a fluence of light in a wavelength range of 290 nm or less irradiated to the plant is less than 20% of that of the light in the wavelength range of 300 nm to 325 nm. Alternatively, the plant is not irradiated with light at any wavelength of 290 nm or less; and then the plant is infected with a microorganism.

14 Claims, 7 Drawing Sheets
(6 of 7 Drawing Sheet(s) Filed in Color)

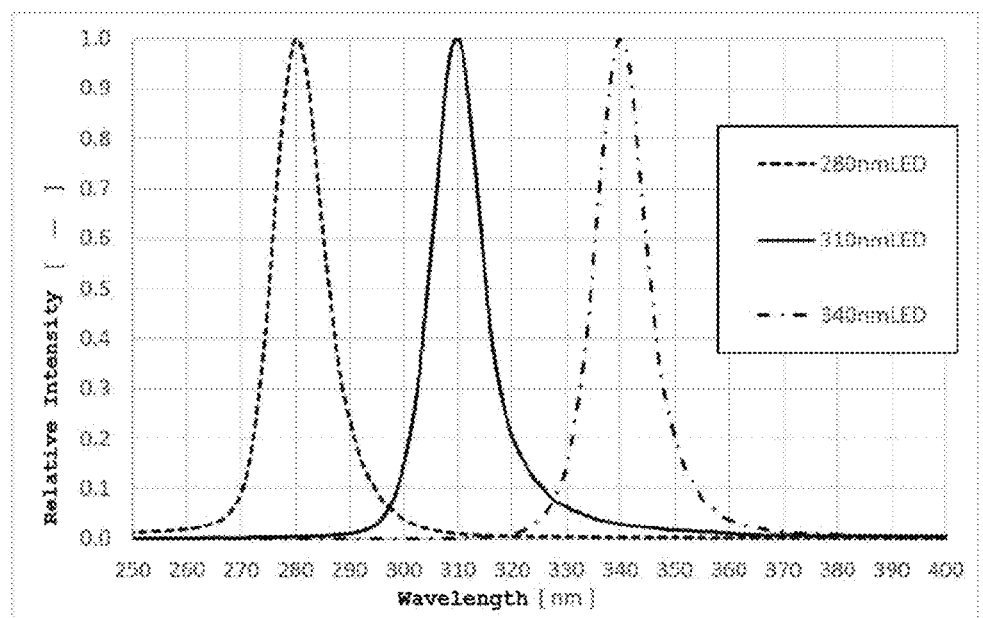
FIG. 3
FIG. 4
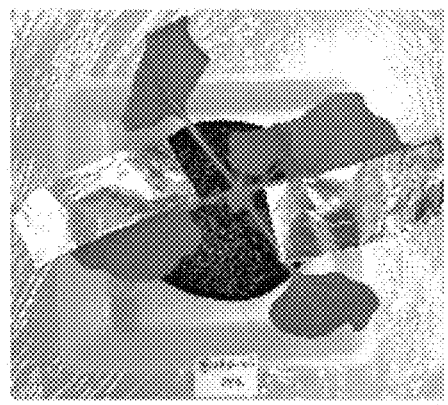 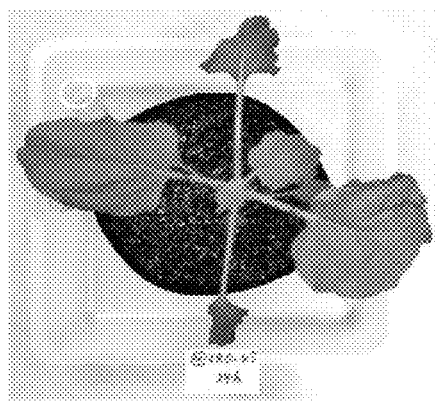
FIG. 5A  FIG. 5B

METHOD OF TREATING PLANT, METHOD OF PRODUCING PLANT INFECTED WITH MICROORGANISM, METHOD OF PRODUCING FERMENTED PLANT PRODUCT, AND PLANT TREATMENT APPARATUS

CROSS-REFERENCE TO RELATED APPLICATIONS

This application claims priority under 35 USC § 119 to Japanese Patent Application No. 2022-173633, filed on Oct. 28, 2022, the contents of which are incorporated herein by reference in their entirety.

TECHNICAL FIELD

The present disclosure relates to a method and an apparatus of treating a plant. More specifically, the present disclosure relates to a method of infecting a plant with a microorganism, a method of producing a plant infected with a microorganism, a method of producing a fermented plant product, and an apparatus for infecting a plant with a microorganism.

BACKGROUND

For introducing a foreign gene into a plant, for example, there are existing techniques for infecting the plant with an infectious agent or microorganism carrying the foreign gene, such as *Agrobacterium*-mediated methods and plant virus vector methods. However, in the conventional known methods, infection of a plant with a microorganism is limited by its resistance to microbial infection.

There is a need for a method of infecting a plant with a useful microorganism more easily and/or efficiently.

SUMMARY

The present disclosure provides, in an aspect, a method of treating a plant (hereinafter also referred to as the "plant treatment method according to the present disclosure"), the method including: irradiating the plant with light in a wavelength range of 300 to 325 nm at a fluence of 4,000 to 50,000 μmol/m$^2$, while a fluence of light in a wavelength range of 290 nm or less irradiated to the plant is less than 20% of the fluence of the light in the wavelength range of 300 to 325 nm, or the plant is not irradiated with light at any wavelength of 290 nm or less; and then infecting the plant with a microorganism.

The present disclosure provides, in another aspect, a method of producing a plant infected with a microorganism (hereinafter also referred to as the "microorganism-infected plant production method according to the present disclosure"), the method including: irradiating a plant with light in a wavelength range of 300 to 325 nm at a fluence of 4,000 to 50,000 μmol/m$^2$, while a fluence of light in a wavelength range of 290 nm or less irradiated to the plant is less than 20% of the fluence of the light in the wavelength range of 300 to 325 nm, or the plant is not irradiated with light at any wavelength of 290 nm or less; and then infecting the plant with the microorganism.

The present disclosure provides, in still another aspect, a method of producing a fermented plant product in a plant (hereinafter also referred to as the "fermented plant product production method according to the present disclosure"), the method including: irradiating the plant with light in a wavelength range of 300 to 325 nm at a fluence of 4,000 to 50,000 μmol/m$^2$, while a fluence of light in a wavelength range of 290 nm or less irradiated to the plant is less than 20% of the fluence of the light in the wavelength range of 300 to 325 nm, or the plant is not irradiated with light at any wavelength of 290 nm or less; infecting the irradiated plant with a microorganism, and then fermenting the infected plant to obtain the fermented plant product.

The present disclosure provides, in still another aspect, a plant treatment apparatus including: a plant holding unit configured to hold a plant; an ultraviolet irradiation unit configured to irradiate at least a portion of the plant held by the plant holding unit with ultraviolet light in a wavelength range of 300 to 325 nm, either without light at any wavelength of 290 nm or less or with light in wavelengths of 290 nm or less at a fluence that is less than 20% of the fluence of the light in the wavelength range of 300 to 325 nm; and a plant immersion unit comprising a tank, the tank being configured to hold a liquid containing a microorganism in a liquid holding space defined within a cavity of the tank, wherein the plant immersion unit is configured to locate the portion of the plant in the liquid holding space, or a liquid ejection unit configured to eject the liquid toward the portion of the plant.

The plant treatment method and/or the plant treatment apparatus according to the present disclosure can infect plants with beneficial microorganisms more easily and/or efficiently than the conventional methods and apparatuses.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 is a diagram showing exemplary emission spectra of three LEDs used in the Examples.

FIG. 4 is a photograph of *Nicotiana benthamiana* before irradiation, with experimental areas defined as (i) an irradiated section irradiated with an LED light (irradiated section) and (ii) an unirradiated section not irradiated with an LED light (unirradiated section), on each of two leaves per plant.

FIGS. 5A and 5B are a set of photographs showing *Nicotiana benthamiana* immediately after (left, FIG. 5A) and 24 hours after (right, FIG. 5B) irradiation with 280 nm-LED light.

DETAILED DESCRIPTION

Figure 1:
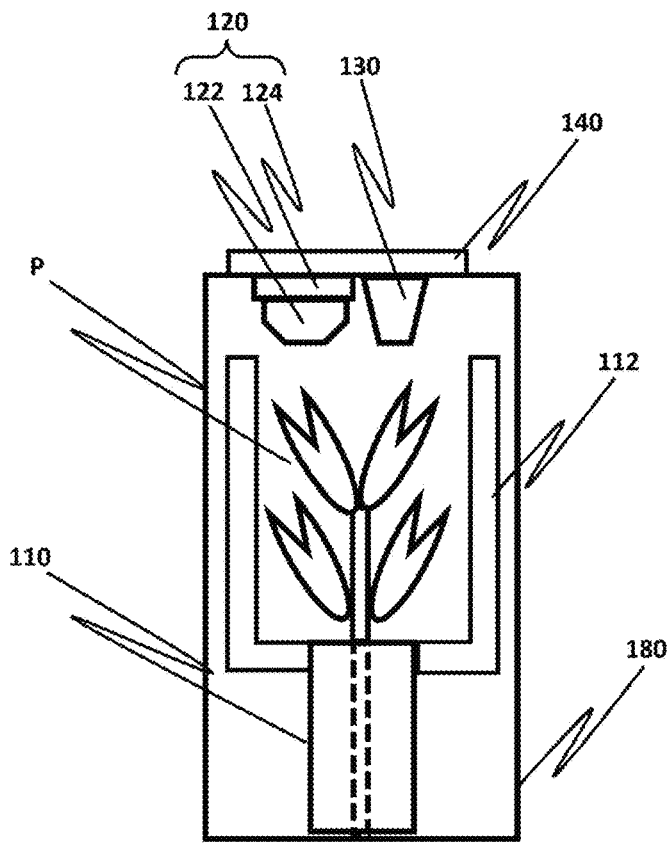
FIG. 1 is an exemplary schematic diagram illustrating an embodiment of an apparatus according to the present disclosure.
Figure 2:
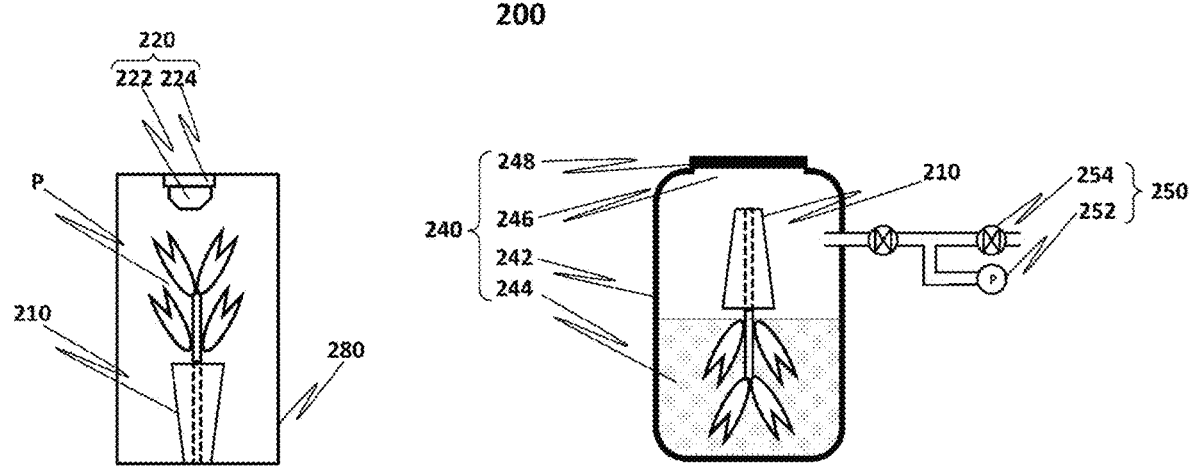
FIG. 2 is an exemplary schematic diagram illustrating another embodiment of an apparatus according to the present disclosure.

Unless defined otherwise, all technical and scientific terms used herein have the same meaning as is commonly understood by one of ordinary skill in the art to which the present disclosure pertains. Although any apparatuses, devices, methods, and materials similar or equivalent to those described herein can be used in the practice or testing according to the present disclosure, representative apparatuses, devices, methods, and materials are now described.

As used herein and the appended claims, the singular forms "a", "an" and "the" include plural referents unless the context clearly dictates otherwise. The terms "comprise", "comprising", "include," "including," "have," "has," "having," and the like are intended to be inclusive and mean that there may be additional elements other than the listed elements.

As used herein, a numerical range "a to b" (where "a" and "b" are specific numerical values) means a range including both end values "a" and "b". In other words, "a to b" is synonymous with "a or greater and b or less", "a or higher and b or lower", or "a or more and b or less" unless it is clear that this is not the case.

The present disclosure is based on a finding that irradiating a plant with light in a wavelength range of 300 to 325 nm (also referred to as "the ultraviolet irradiation treatment according to the present disclosure") can transiently reduce the resistance of the plant to microbial infection.

<Plant Treatment Method and Microorganism-Infected Plant Production Method>

The plant treatment method according to the present disclosure includes:
  irradiating the plant with light in a wavelength range of 300 to 325 nm at a fluence of 4,000 to 50,000 µmol/m$^2$, while a fluence at wavelengths of 290 nm or less irradiated to the plant is less than 20% of the fluence of the light in the wavelength range of 300 to 325 nm, or the plant is not irradiated with light at any wavelength of 290 nm or less; and then
  infecting the plant with a microorganism.

The microorganism-infected plant production method according to the present disclosure includes:
  irradiating a plant with light in a wavelength range of 300 to 325 nm at a fluence of 4,000 to 50,000 µmol/m$^2$, while a fluence at wavelengths of 290 nm or less irradiated to the plant is less than 20% of the fluence of the light in the wavelength range of 300 to 325 nm, or the plant is not irradiated with light at any wavelength of 290 nm or less; and then
  infecting the plant with the microorganism.

Hereinafter, the "plant treatment method according to the present disclosure," the "microorganism-infected plant production method according to the present disclosure," and the "fermented plant product production method according to the present disclosure" may be collectively referred to as the "methods according to the present disclosure."

(Plant)

As used herein, a plant is not particularly limited as long as it can be infected with a microorganism or infectious agent to be used. The plant may be a dicotyledon or a monocotyledon. Examples of dicotyledons include plants belonging to the family Solanaceae, in particular the genera *Nicotiana* and *Solanum*; the family Brassicaceae, in particular the genera *Brassica, Raphanus*, and *Arabidopsis*; the family Rosaceae, in particular the genus *Fragaria*; the family Astraceae, in particular the genus *Lactuca*; the family Cucurbitaceae, in particular the genera *Cucumis* and *Cucurbita*; the family Fabaceae, in particular the genera *Glycine, Vigna, Phaseolus, Vicia*, and *Arachis*; the family Rutaceae, in particular the genus *Citrus*; the family Vitaceae, in particular the genus *Vitis*; the family Lamiaceae, in particular the genus *Perilla*; and the family Theaceae, in particular the genus *Camellia*. Examples of monocotyledons include plants belonging to the family Poaceae, in particular the genera *Oryza, Triticum, Hordeum, Secale, Zea*, and *Saccharum*.

The ultraviolet irradiation treatment according to the present disclosure can transiently reduce the microbial resistance of the irradiated plant, in other words, it can transiently enhance the infection efficiency of microbes to the plant. Thus, plants having a low infection efficiency in conventional microbial infection methods, particularly *Agrobacterium*-mediated methods, such as plants of the families Poaceae and Fabaceae, can be also efficiently infected with microorganisms after subjecting to the ultraviolet irradiation treatment. These plants can therefore be used in the methods according to the present disclosure.

The plant is preferably selected from the plants belonging to the families Solanaceae, Brassicaceae, Astraceae, Rosaceae, Fabaceae, and Poaceae, more preferably selected from the plants belonging to the families Solanaceae, Rosaceae, Fabaceae, and Poaceae, more preferably selected from the plants belonging to the families Solanaceae and Rosaceae, and more preferably selected from the plants belonging to the family Solanaceae, with the genus *Nicotiana* plants being further preferred.

Specific examples of plants belonging to the genus *Nicotiana* include *Nicotiana tabacum*, *N. benthamiana*, *N. alata*, *N. glauca*, and *N. longiflora*, with *N. benthamiana* being particularly preferred.

Specific examples of plants, other than those belonging to the genus *Nicotiana*, that can be used in the methods according to the present disclosure include *Solanum melongena*, *Solanum lycopersicum*, *Solanum tuberosum*, *Brassica oleracea* var. *botrytis*, *Brassica oleracea* var. *capitata*, *Brassica oleracea* var. *italica*, *Brassica rapa* var. *perviridis*, *Brassica rapa* var. *chinensis*, *Brassica rapa* var. *nipposinica*, *Brassica rapa* var. *rapa*, *Brassica rapa* var. *glabra*, *Brassica campestris*, *Brassica napus*, *Brassica juncea*, *Raphanus sativus*, *Arabidopsis thaliana*, *Cucumis sativus*, *Cucurbita moschata*, *Cucurbita mamima*, *Cucurbita pepo*, *Fragaria* x *ananassa* Duchesne ex Rozier, *Lactuca sativa*, *Saccharum officinarum*, *Vigna angularis*, *Phaseolus vulgaris*, *Vicia faba*, *Arachis hypogaea*, *Perilla frutescens* var. *crispa*, *Oryza sativa*, *Triticum aestivum*, *Triticum durum*, *Hordeum vulgare*, *Secale cereale*, *Zea mays*, *Saccharum officinarum*, *Vitis* spp., and *Camellia sinensis*.

In some embodiments, the plant is a plant that can be infected with *Agrobacterium*. In some other embodiments, the plant is a plant that can be infected with a plant virus.

In the present specification, the plant may be the whole plant, and it may also refer to a part(s) of the plant, a cultured plant cell(s), including cultured cells in the form of callus, or even a crushed material of the whole plant or a part(s) thereof, unless the context clearly indicates that it is not. A part(s) of the plant may be a root, stem, leaf, flower, bud, seed, or any combination thereof.

The plant may be a plant under cultivation or a plant temporarily suspended from being cultivated. Cultivation may be soil cultivation, more specifically outdoor cultivation or greenhouse cultivation, or may be nutrient solution cultivation, more specifically hydroponics, spray cultivation, or solid medium cultivation. Cultivation of the plant temporarily suspended from being cultivated can be resumed during or after the application of the methods according to the present disclosure. The plant may also be a plant after harvesting.

(Irradiation Step)

In the irradiation step, a plant is irradiated with light in a wavelength range of 300 to 325 nm.

A lower limit of a fluence (or irradiation amount) of light in the wavelength range of 300 to 325 nm can be no less than 4,000 $\mu mol/m^2$, more specifically no less than 4,500 $\mu mol/m^2$, more specifically no less than 5,000 $\mu mol/m^2$, more specifically no less than 5,500 $\mu mol/m^2$, more specifically no less than 6,000 $\mu mol/m^2$, more specifically no less than 6,500 $\mu mol/m^2$, and more specifically 6,750 $\mu mol/m^2$. Irradiation of a plant with light in the wavelength range of 300 to 325 nm at a fluence of less than 4,000 $\mu mol/m^2$ may not be able to reduce the resistance of the irradiated plant to microbial infection.

An upper limit of a fluence of light in the wavelength range of 300 to 325 nm can be no more than 50,000 $\mu mol/m^2$, more specifically no more than 47,500 $\mu mol/m^2$, more specifically no more than 45,000 $\mu mol/m^2$, more specifically no more than 42,500 $\mu mol/m^2$, more specifically no more than 40,000 $\mu mol/m^2$, more specifically no more than 37,500 $\mu mol/m^2$, more specifically no more than 35,000 $\mu mol/m^2$, and more specifically 33,750 $\mu mol/m^2$. Irradiation with light in the wavelength range of 300 to 325 nm at a fluence of more than 50,000 $\mu mol/m^2$ may be likely to cause any damage to the irradiated plant.

Ranges of fluence of light in the wavelength range of 300 to 325 nm can include any combination of the lower and upper limits listed above. Specific ranges include, but not limited to, from 4,000 $\mu mol/m^2$ to 50,000 $\mu mol/m^2$, from 4,000 $\mu mol/m^2$ to 47,500 $\mu mol/m^2$, from 4,500 $\mu mol/m^2$ to 47,500 $\mu mol/m^2$, from 4,500 $\mu mol/m^2$ to 45,000 $\mu mol/m^2$, from 5,000 $\mu mol/m^2$ to 45,000 $\mu mol/m^2$, from 5,000 $\mu mol/m^2$ to 42,500 $\mu mol/m^2$, from 5,500 $\mu mol/m^2$ to 42,500 $\mu mol/m^2$, from 6,000 $\mu mol/m^2$ to 42,500 $\mu mol/m^2$, from 6,000 $\mu mol/m^2$ to 40,000 $\mu mol/m^2$, from 6,500 $\mu mol/m^2$ to 40,000 $\mu mol/m^2$, from 6,500 $\mu mol/m^2$ to 37,500 $\mu mol/m^2$, from 6,750 $\mu mol/m^2$ to 37,500 $\mu mol/m^2$, from 6,750 $\mu mol/m^2$ to 35,000 $\mu mol/m^2$, and from 6,750 $\mu mol/m^2$ to 33,750 $\mu mol/m^2$.

Because DNA and RNA have an absorption maximum at around 260 nm wavelength, it is concerned that light at around 260 nm wavelength may have a noticeable adverse effect to plants. Light in a wavelength range of 280 to 290 nm may also have an inhibitory effect on viral infection in tomato seedlings, for example. Therefore, at least during the irradiation with light in the wavelength range of 300 to 325 nm, the plant is not irradiated with light at any wavelength of 290 nm or less, or if irradiated, a fluence at wavelengths of 290 nm or less irradiated to the plant is set to be less than 20%, preferably less than 10%, more preferably less than 5%, and more preferably less than 1%, of the fluence of light in the wavelength range of 300 to 325 nm.

Light in a wavelength range of 330 nm or more does not contribute to reduction of the microbial infection resistance of the plant. Therefore, in view of energy efficiency, at least during the irradiation with light in the wavelength range of 300 to 325 nm, the plant is not irradiated with light at any wavelength of 330 nm or more, or if irradiated, a fluence of light at wavelengths of 330 nm or more irradiated to the plant may be, for example, less than 50%, preferably less than 30%, more preferably less than 20%, more preferably less than 10%, more preferably less than 5%, and still more preferably less than 1%, of the fluence of light in the wavelength range of 300 to 325 nm.

The light in the wavelength range of 300 to 325 nm can be irradiated at a photon flux density of 0.05 to 300 $\mu mol/m^2/s$, for example. Irradiation of a plant with light in the wavelength range of 300 to 325 nm at a photon flux density of less than 0.05 $\mu mol/m^2/s$ may not be able to reduce the resistance of the irradiated plant to microbial infection. Irradiation with light in the wavelength range of 300 to 325 nm at a photon flux density of more than 300 $\mu mol/m^2/s$ may cause any damage to the irradiated plant. Preferably, the light in the wavelength range of 300 to 325 nm is irradiated at a photon flux density of 0.1 to 300 $\mu mol/m^2/s$, more preferably 0.2 to 200 $\mu mol/m^2/s$, more preferably 0.5 to 100 $\mu mol/m^2/s$, more preferably 0.5 to 50 $\mu mol/m^2/s$, more preferably 1 to 20 $\mu mol/m^2/s$, more preferably 1 to 15 $\mu mol/m^2/s$, more preferably 2 to 15 $\mu mol/m^2/s$, and more preferably 2 to 10 $\mu mol/m^2/s$.

A light source used in the methods according to the present disclosure is not particularly limited as long as it is capable of emitting light in the wavelength range of 300 to 325 nm, and may be, for example, any commonly used ultraviolet light source such as a UV lamp. Examples of UV lamps may include light-emitting diodes (LEDs), laser diodes (LDs), xenon lamps, fluorescent lamps, incandescent lamps, metal hydride lamps, and high-pressure mercury lamps. As ultraviolet light, light extracted from the sunlight using an optical filter or the like can be used.

In a case where a light source used emits, in addition to light in the wavelength range of 300 to 325 nm, light in a wavelength range of 290 nm or less at a photon flux density that is 20% or more of the photon flux density of the light in the wavelength range of 300 to 325 nm, a filter having a transmittance that is higher for the light in the wavelength range of 300 to 325 nm than for the light in the wavelength range of 290 nm or less may be used together with the light source, so that the photon flux density of the light in the wavelength range of 290 nm or less irradiated to the plant is less than 20%, or more specifically less than 15%, 10%, 5%, or 1%, of the photon flux density of the light in the wavelength range of 300 to 325 nm.

Additionally or alternatively, in a case where a light source used emits, in addition to light in the wavelength range of 300 to 325 nm, light in the wavelength range of 330 nm or more at a photon flux density that is 50% or more of the photon flux density of the light in the wavelength range of 300 to 325 nm, a filter having a transmittance that is higher for the light in the wavelength range of 300 to 325 nm than for the light in the wavelength range of 330 nm or more may be used together with the light source, so that the photon flux density of the light in the wavelength range of 330 nm or more irradiated to the plant is less than 50%, or more specifically less than 40%, 30%, 25%, 20%, 15%, 10%, or 5%, of the photon flux density of the light in the wavelength range of 300 to 325 nm.

In view of energy efficiency, the irradiated light in the wavelength range of 300 to 325 nm has the main peak wavelength of, for example, 310±7 nm, preferably 310±5 nm, and more preferably 310±3 nm. It is preferable that no second peak is present in wavelengths of 300 to 325 nm or the intensity of the second peak, if any, is one-tenth (1/10) or less of that of the main peak. As used herein, the term "main peak wavelength" refers to the peak wavelength at which the intensity is maximum in its spectrum. In the context of light having a single peak, such as LED light, the term "peak wavelength" is synonymous with "main peak wavelength."

A full width at half maximum of the main peak within wavelengths of 303 to 317 nm, preferably within wavelengths of 305 to 315 nm, and more preferably within wavelengths of 303 to 313 nm, is for example 1 to 15 nm, preferably 5 to 15 nm, and more preferably 5 to 10 nm. The use of light having a full width at half maximum of the main peak of 15 nm or less makes it possible to selectively irradiate light in a wavelength range effective for reducing the plant's resistance to microbial infection while avoiding irradiation of light in a wavelength range that does not contribute to reducing the plant's resistance to microbial infection, and also further improves energy efficiency. Light having a full width at half maximum of the main peak of less than 1 nm can also be used in the methods according to the present disclosure; however, in view of cost efficiency, it is currently preferable to use light having a full width at half maximum of the main peak of 1 nm or more. Therefore, specific examples of light in a wavelength range of 300 to 325 nm can include light having a wavelength spectrum with a peak wavelength of 310±7 nm and a full width at half maximum in a range of 1 to 15 nm, more specifically a full width at half maximum in a range of 5 to 15 nm, and more specifically a full width at half maximum in a range of 5 to 10 nm; light having a wavelength spectrum with a peak wavelength of 310±5 nm and a full width at half maximum in a range of 1 to 15 nm, more specifically a full width at half maximum in a range of 5 to 15 nm, and more specifically a full width at half maximum in a range of 5 to 10 nm; and light having a wavelength spectrum with a peak wavelength of 310±3 nm and a full width at half maximum in a range of 1 to 15 nm, more specifically a full width at half maximum in a range of 5 to 15 nm, and more specifically a full width at half maximum in a range of 5 to 10 nm.

The light source of light in a wavelength range of 300 to 325 nm is particularly preferably a light emitting diode (LED) or a laser diode (LD) having a single peak in the light emission spectrum. The use of an LED or LD as a light source can easily achieve selective irradiation with light in a wavelength range effective to reduce the plant's resistance to microbial infection while avoiding irradiation with light in a wavelength range that does not contribute to reducing the plant's resistance to microbial infection and may have adverse effect on the plant. The use of an LED or LD is also preferred in terms of energy efficiency and economy due to its low heat generation, low power consumption and long life. In addition, the use of an LED or LD can facilitate the control of fluence and/or photon flux density.

An LED or LD capable of emitting light in a wavelength range of 300 to 325 nm can be formed of, for example, an AlGaN- or InAlGaN-based material.

The fluence of light in a wavelength range of 300 to 325 nm to a plant can be adjusted to 4,000 to 50,000 µmol/m$^2$ by, for example, controlling switching on and off the light source (if the plant is stationary, for example) or controlling the time required for the plant to pass through the irradiation area (if the plant is transported by a conveyor, for example).

Light in a wavelength range of 300 to 325 nm may be irradiated to a plant as continuous light, intermittent light, or a combination thereof. It is preferable that the light in the wavelength range of 300 to 325 nm is intermittently irradiated. The use of intermittent light can avoid or reduce the temperature rise of the irradiated plant and/or the light source. Specific examples of the intermittent light include those with a pulse width of 100 ms or less, more specifically 50 ms or less, more specifically 20 ms or less, more specifically 10 ms or less, and more specifically 5 ms or less, and a duty ratio of 50% or less, more specifically 40% or less, more specifically 30% or less, more specifically 20% or less, more specifically 10% or less, and more specifically 5% or less.

During irradiation with light in the wavelength range of 300 to 325 nm, the plant may be stationary or in motion. The plant, if it is a plant part(s), or a crushed material of the whole plant or a part(s) thereof, may be, for example, rotated, vibrated, floated, or stirred. The plant may be irradiated with light while being transported.

The light may be irradiated from one direction or from two or more directions.

The light in the wavelength range of 300 to 325 nm is not necessarily irradiated to the whole of the plant held by a plant holding unit, and may be irradiated to one or more parts or areas of the plant so long as it is irradiated at a fluence needed. The light in the wavelength range of 300 to 325 nm may be irradiated to a limited desired part(s) of the plant, such as flowers and/or flower buds (stiff and/or swollen buds), roots or the like, so as not to affect the resistance of the other parts of the plant to microbial infection, making it possible to avoid an unnecessary increase in the risk of infectious diseases in the plant. Irradiation limited to a desired part(s) can also reduce the wilting of the plant.

Irradiation with light in a wavelength range of 300 to 325 nm is preferably performed in a dark place. As used herein, the term "dark place" refers to a place in which a photon flux density in the photosynthetically active wavelength range, i.e., at wavelengths of 400 to 700 nm (hereinafter referred to as the "photosynthetically active photon flux density"), does not cause photosynthesis in cells of the plant, more specifically, a photosynthetically active photon flux density of ≤10 µmol/m²/s.

Placing the plant in a dark place during irradiation with light in a wavelength range of 300 to 325 nm, i.e., not allowing photosynthesis to occur in cells of the plant, can efficiently induce a decrease in the resistance of the plant to microbial infection.

(Infection Step)

In the infection step, the plant irradiated with light in a wavelength range of 300 to 325 nm is infected with a microorganism.

The microorganism is not particularly limited as long as it can infect cells of the plant used in the methods according to the present disclosure, which cells have been irradiated with light in the wavelength range of 300 to 325 nm and reduced the resistance to microbial infection compared to before irradiation. Of course, the microorganism may be a microorganism that can infect the cells before irradiation with light in the wavelength range of 300 to 325 nm and having normal resistance to microbial infection. In the present specification, "microorganism" is intended to include bacteria, fungi such as yeast and filamentous fungi, and viruses, as well as virus vectors (which can also be referred to as "infectious agents"). In the present specification, "microorganism" and "infectious agent" are used interchangeably with regard to infection to plants.

In some embodiments, the microorganism is an endophyte or endosymbiotic bacterium. Endophyte are not particularly limited as long as they are capable of endosymbiosis with the plant to be used and can be either bacterial or fungal endophytes.

Bacterial endophytes can be rhizobia, for example bacteria of a genus selected from the genera *Rhizobium, Bradyrhizobium, Sinorhizobium*, and *Mesorhizobium*. Bacterial endophytes herein include bacteria of the genus *Rugamonas*. Bacteria of the genus *Rugamonas* are endophytic bacteria of barley (root) and can produce a growth-promoting effect in infected plants.

Fungal or filamentous endophyte can be mycorrhizal fungi. Mycorrhizal fungi can be, for example, arbuscular mycorrhizal fungi (AM or VA fungi) or ericoid mycorrhizal fungi. Arbuscular mycorrhizal fungi can be, for example, fungi of a genus selected from the genera *Giga-spora, Glomus*, and *Rhizophagus*. Ericoid mycorrhizal fungi can be, for example, fungi of a genus selected from the genera *Neotyphodium* and *Epichloe*.

Endophyte-infected plants may have enhanced immunity, accelerated growth, and/or increased tolerance to environmental stresses such as, for example, strong light, high temperature, and/or drought, resulting in increased yield.

Thus, in embodiments where the microorganism is an endophyte, the plant treatment method according to the present disclosure can be considered as a method of increasing plant yield.

Therefore, the present disclosure provides a method of increasing a yield of a plant, the method including:
irradiating the plant, in particular a root or roots thereof, with light in a wavelength range of 300 to 325 nm at a fluence of 4,000 to 50,000 µmol/m², while a fluence at wavelengths of 290 nm or less irradiated to the plant is less than 20% of that of the light in the wavelength range of 300 to 325 nm, or the plant is not irradiated with light at any wavelength of 290 nm or less; and then
infecting the plant, in particular the root or roots, with an endophyte.

In embodiments where the microorganism is an endophyte, the microorganism-infected plant production method according to the present disclosure can be considered as a method of producing an endophyte-infected plant.

Therefore, the present disclosure provides a method of producing a plant infected with an endophyte, the method including:
irradiating a plant with light in a wavelength range of 300 to 325 nm at a fluence of 4,000 to 50,000 µmol/m², while a fluence at wavelengths of 290 nm or less irradiated to the plant is less than 20% of that of the light in the wavelength range of 300 to 325 nm, or the plant is not irradiated with light at any wavelength of 290 nm or less; and then
infecting the plant with the endophyte.

In some embodiments, the microorganism is a microbial pesticide. Microbial pesticides are used as insecticides, nematicides, or fungicides to control plant pests.

Examples of microbial pesticides that are bacteria include, for example, *Bacillus thuringiensis, Pasteuria penetrans, Rhizobium radiobacter* or *Agrobacterium tumefaciens, Pseudomonas fluorescens, Pseudomonas rhodesiae, Bacillus amyloliquefaciens, Bacillus subtilis, Bacillus simplex, Variovorax paradoxus, Lactiplantibacillus plantarum*, and *Erwinia carotovora* subsp. *carotovora*. Examples of microbial pesticides that are filamentous fungi include, for example, *Verticillium lecanii, Paecilomyces tenuipes, Paecilomyces fumosoroseus, Beauveria bassiana, Beauveria brongniartii, Metarhizium anisopliae, Coniothyrium minitans, Talaromyces flavus*, and *Tricoderma atroviride*. Examples of microbial pesticides that are viruses include, for example, Nuclear Polyhedrosis viruses (NVP) and Granulosis viruses (GV) of the genus *Baculovirus*, and cytoplasmic polyhedrosis viruses of the genus *Cypovirus*, specifically *Baculovirus homona magnanima* granulosis virus, *Apple Adoxophyes orana* granulosis virus, and *Spodoptera litura* nuclear polyhedrosis virus.

The use of a microbial pesticide as a microorganism in the plant treatment method according to the present disclosure makes it possible for the microbial pesticide to act efficiently on the plant. Specifically, a time needed for the microbial pesticide to colonize in the plant can be shortened and/or an amount of the microbial pesticide used can be reduced. In addition, the plants infected with pesticidal microorganisms may have increased resistance to pests, resulting in increased yield.

Thus, in embodiments where the microorganism is a microbial pesticide, the plant treatment method according to the present disclosure can be considered as a method of increasing a yield of a plant and/or controlling a pest in the plant.

Therefore, the present disclosure provides a method of increasing plant yield and/or controlling pests in a plant, the method including:
irradiating the plant with light in a wavelength range of 300 to 325 nm at a fluence of 4,000 to 50,000 µmol/m², while a fluence at wavelengths of 290 nm or less irradiated to the plant is less than 20% of that of the light in the wavelength range of 300 to 325 nm, or the plant is not irradiated with light at any wavelength of 290 nm or less; and then
infecting the plant with a microorganism that can act as a microbial pesticide on the plant.

In addition, in embodiments where the microorganism is a microbial pesticide, the microorganism-infected plant production method according to the present disclosure can be considered as a method of producing a plant with increased resistance to a pest.

Therefore, the present disclosure provides a method of producing a plant having increased pest resistance, the method including:

irradiating a plant with light in a wavelength range of 300 to 325 nm at a fluence of 4,000 to 50,000 μmol/m², while a fluence at wavelengths of 290 nm or less irradiated to the plant is less than 20% of that of the light in the wavelength range of 300 to 325 nm, or the plant is not irradiated with light at any wavelength of 290 nm or less; and then infecting the plant with a microorganism that can act as a microbial pesticide on the plant.

Examples of pests include, for example, moth of the family Tortricidae, *Spodoptera litura*, lice, thrips, whiteflies, aphids, spider mites, *Plutella xylostella, Pieris rapae, Helicoverpa armigera*, mites, scale insects, longcorns, *Ostrinia fur nacalis, Mamestra brassicae, Hellulla undalis, Acroleopsis sapporensis, Spodoptera exigua*, and *Meloidogyne incognita*.

Examples of plant diseases caused by pests include powdery mildew, cucumber mosaic, fusarium wilt, sclerotinia rot, white rot, gray mold, leaf mold, fruit mold, root anthracnose, bacterial gall, bacterial grain rot, bacterial seedling blight, bacterial brown stripe, "Bakanae" disease, blast, seedling blight, violet-root rot, southern blight, crown gall, bud blight, bacterial soft rot, black rot, bacterial spot, bacterial black spot, bacterial soft rot, bacterial stem necrosis, bacterial shot hole, canker, bacterial shoot blight, white scab, leaf blotch, leaf blight, black leaf blight, spot blotch, brown spot, white rust, scab, bacterial wilt, and fusarium root rot. Increased pest resistance can reduce occurrence of one or more of the plant diseases.

In some embodiments, the bacterium is able to transfer its DNA molecule, e.g., at least a part of a plasmid carried by the bacterium, into the infected plant, for example, in the genome of the plant. In certain embodiments, the microorganism is an *Agrobacterium*. The *Agrobacterium* is preferably a tumorigenic *Agrobacterium* (*Rhizobium radiobacter* or *Agrobacterium tumefaciens*) or a rooting *Agrobacterium* (*Rhizobium rhizogenes* or *Agrobacterium rhizogenes*).

In some embodiments, the microorganism or infectious agent is a plant virus vector.

The plant virus vector is a plant virus-based vector. The plant virus is not particularly limited as long as it can infect cells of the plant used in the methods according to the present disclosure, which cells have been irradiated with light in the wavelength range of 300 to 325 nm and reduced the resistance to microbial infection compared to before irradiation. The plant virus can be, for example, a virus of a genus selected from the genera *Tobamovirus, Potexvirus, Potyvirus, Tobravirus, Tombusvirus, Cucumovirus, Bromovirus, Alfamovirus, Comovirus, Carmovirus, Cheravirus, Waikavirus*, and *Caulimovirus*. The plant virus is preferably a positive-sense single-stranded plant RNA virus.

Specific examples of plant virus vectors include cauliflower mosaic virus (CaMV) vectors, cucumber mosaic virus (CMV) vectors, tobacco mosaic virus (TMV) vectors, potato X virus (PVX) vectors, tomato mosaic virus (ToMV) vectors, plum pox virus (PPV) vectors, alfalfa mosaic virus (AIMV) vectors, coupea mosaic virus (CPMV) vectors, and zucchini yellow mosaic virus (ZYMV) vectors.

The microorganism may be a wild type or genetically engineered microorganism.

In some embodiments, the microorganism carries a gene encoding a polypeptide or protein of interest to be expressed in the plant used in the methods according to the present disclosure. The gene is foreign to the plant. In the infection step, the plant is infected with a microorganism carrying a foreign gene of interest so that the foreign gene can be introduced into the plant. In this case, the "infection step" can be also referred to as "foreign gene transfer step".

The plant having an introduced foreign gene (i.e., transgenic plant) may transiently express the polypeptide or protein of interest (in this case, the plant can be also referred to as a transient transformant or transfectant) or stably express it ("transgenic plant" or "genetically-modified plant" in narrow sense).

Thus, in embodiments where the microorganism is a microorganism carrying a foreign gene of interest, the plant treatment method according to the present disclosure can be considered as a method of introducing a foreign gene into a plant.

Therefore, the present disclosure provides a method of introducing a foreign gene into a plant, the method including:

irradiating the plant with light in a wavelength range of 300 to 325 nm at a fluence of 4,000 to 50,000 μmol/m², while a fluence at wavelengths of 290 nm or less irradiated to the plant is less than 20% of that of the light in the wavelength range of 300 to 325 nm, or the plant is not irradiated with light at any wavelength of 290 nm or less; and then infecting the plant with a microorganism carrying the foreign gene.

In embodiments where the microorganism is a microorganism carrying a foreign gene, the microorganism-infected plant production method according to the present disclosure can be considered as a method of producing a plant having an introduced foreign gene.

Therefore, the present disclosure provides a method of producing a plant having a foreign gene introduced, the method including:

irradiating the plant with light in a wavelength range of 300 to 325 nm at a fluence of 4,000 to 50,000 μmol/m², while a fluence at wavelengths of 290 nm or less irradiated to the plant is less than 20% of that of the light in the wavelength range of 300 to 325 nm, or the plant is not irradiated with light at any wavelength of 290 nm or less; and then infecting the plant with a microorganism carrying the foreign gene.

The polypeptide or protein of interest to be expressed in the plant can be any polypeptide or protein, for example, a medically or industrially useful polypeptide, as long as it can be expressed in the plant used. More specifically, the polypeptide or protein of interest can be, for example, an immunogenic or antigenic polypeptide or protein from a pathogen such as a virus, an antibody or a binding fragment thereof, a cytokine, an enzyme, a growth factor, or any other bioactive protein or a functional fragment thereof. Particularly preferably, the immunogenic or antigenic polypeptide or protein is such a polypeptide or protein that is able to elicit a neutralizing antibody, for example, such a polypeptide or protein that can be used as a vaccine, including a VLP vaccine.

The foreign gene may be contained in an expression cassette. In the expression cassette, the foreign gene may be operably linked upstream to a promoter suitable for the plant used. Examples of promoters include, but are not limited to, the 35S promoter of cauliflower mosaic virus and the ubiquitin promoter of *Zea mays*. The expression cassette may contain another expression regulatory element(s) including a terminator.

The infection of the plant with a microorganism can be performed by bringing a suspension of the microorganism (hereinafter also referred to as "microorganism suspension") into contact with the plant. A liquid in which the microorganism is suspended can be a culture medium suitable for the microorganism, which medium may contain a surfactant or detergent. The microorganism suspension that came into contact with the plant then infiltrates plant tissues, thereby infecting cells of the plant with the microorganism. The contact between the microorganism suspension and the plant can be made, more specifically, by application or spraying of the microorganism suspension onto the plant or by immersion of the plant in the microorganism suspension. Alternatively, the microorganism suspension may be injected into the plant using a syringe, for example, thereby infiltrating it into the plant tissues.

Alternatively, infection can be performed by bringing the plant into contact with dried powder obtained by freeze-drying or spray-drying the microorganism suspension, e.g., a hydrate, driftless (DL) powder, or flow dust (FD) agent or powder. In this case, the contact can be performed by, for example, spraying the powder or by dispersing the powder by using an air blowing mechanism (also referred to as blowing body) provided in a greenhouse, for example.

The microorganism suspension need not be brought into contact with the whole plant, but can be brought into contact with a part(s) of the plant, such as all or some leaves of the plant, the whole leaf or a portion thereof, the whole root or a portion thereof, all or some aerial parts of the plant, or the whole flower and/or bud or a portion thereof. As used herein, "aerial parts" can be leaves and/or stems, and may optionally include flowers and/or buds.

In a case where the infection is performed by immersing the plant in the microorganism suspension, the plant may be subjected to pressure reduction treatment during immersion to promote infiltration of the microorganism suspension into the plant tissues. A target reduced pressure can be, for example, a pressure of 0.005 to 0.5 atm, more specifically 0.005 to 0.3 atm, more specifically 0.01 to 0.3 atm, more specifically 0.01 to 0.2 atm, more specifically 0.01 to 0.1 atm, and more specifically 0.02 to 0.1 atm. Alternatively, the target pressure can be, for example, a pressure of 0.5 to 50 kPa, more specifically 0.5 to 30 kPa, more specifically 1 to 30 kPa, more specifically 1 to 20 kPa, more specifically 1 to 10 kPa, and more specifically 2 to 10 kPa. A duration of reduced pressure is, for example, 10 seconds to 10 minutes, more specifically 10 seconds to 5 minutes, more specifically 20 seconds to 5 minutes, more specifically 20 seconds to 3 minutes, more specifically 30 seconds to 3 minutes, and more specifically 30 seconds to 2 minutes.

After the pressure reduction treatment, the pressure is restored to atmospheric or near ambient pressure. The time required for restoration is not particularly limited and can be, for example, 10 seconds or less, more specifically 5 seconds or less, more specifically 3 seconds or less, and more specifically 1 second or less.

Specific examples of methods of infecting the plant with the microorganism include known *Agrobacterium*-mediated methods (also called agroinfiltration methods; including vacuum infiltration methods), floral spray methods, floral dip methods, and plant virus vector methods.

The infection step is preferably performed in a dark place. By placing the plant in the dark place during the infection step, not allowing photosynthesis to occur in the plant cells, the reduced resistance to microbial infection, caused by the irradiation step, can be maintained throughout the infection step, thus achieving efficient infection. More preferably, the plant is placed in the dark place from the beginning of the irradiation step at the latest until the end of the infection step at the earliest.

After the infection step, any remaining microorganisms on the plant surface may be removed using water, or sterile/sterilized water, such as a 70% ethanol solution, for example.

(Dark Place Storage Step)

The plant infected with the microorganism in the infection step may then be placed in a dark place.

By placing the plant in the dark place after the infection step, the reduced resistance to microbial infection, caused by the irradiation step, can be maintained, allowing a greater percentage of the microorganisms infiltrated into the plant tissues in the infection step, to infect the plant cells.

An upper limit of a period during which, after the contact with the microorganism suspension or dried powder thereof, the plant is placed in the dark place is not particularly limited, and can be, for example, 48, 36, 24, 18, or 12 hours. A lower limit of that period is not particularly limited, and can be, for example, 5 minutes, 15 minutes, 30 minutes, 1 hour, 2 hours, 3 hours, 4 hours, 5 hours, or 6 hours. The period of placing in the dark place can include any combination of the lower and upper limits listed above.

Specific examples of periods of placing in the dark place include, but are not limited to, from 5 minutes to 48 hours, from 15 minutes to 48 hours, from 30 minutes to 48 hours, from 1 to 48 hours, from 2 to 48 hours, from 3 to 48 hours, from 6 to 48 hours, from 6 to 36 hours, from 6 to 24 hours, from 6 to 18 hours, or from 6 to 12 hours.

Preferably, the plant is placed in the dark place from the beginning of the infection step at the latest, and more preferably from the beginning of the irradiation step at the latest.

(Plant Growth Step or Cultivation Step)

The plant infected with the microorganism in the infection step may then be grown.

The plant can be grown by any known cultivation method, and thus the plant growth step may be also referred to as cultivation step.

Cultivation may be soil cultivation, more specifically outdoor cultivation or greenhouse cultivation, or may be nutrient solution cultivation, more specifically hydroponics, spray cultivation, or solid medium cultivation. The nutrient solution cultivation can be performed under aseptic conditions.

The cultivation, especially nutrient solution cultivation, may be performed in a controlled environment. Environmental conditions to be controlled include, for example, light and dark cycle, temperature, humidity, fluence of natural light and/or artificial light, and carbon dioxide concentration. These conditions are not particularly limited as long as they are suitable for the cultivation/growth of the plant used.

The light and dark cycle can be appropriately selected according to the plant to be cultivated and its growth stage. The light and dark cycle can be a long-day condition of, for example, 14 to 18 hours light, or a short-day condition of, for example, 6 to 10 hours light. A light source of artificial light is not limited as long as it can be used for the cultivation of the plant used, and can be, for example, an incandescent lamp, a fluorescent lamp, a white lamp, a high intensity discharge (HID) lamp, such as a high pressure sodium lamp, a metal halide lamp, a high pressure mercury lamp, an LED, such as a white LED, a cold cathode fluorescent lamp (CCFL), an organic EL lamp, or the like. The artificial light is irradiated at a photosynthetically active photon flux density that is adjusted appropriately according to the plant to be cultivated and its stage of growth. The photosynthetically active photon flux density can be, for example, 50 to 600 µmol/m²/s, and more specifically 100 to 500 µmol/m²/s.

The temperature can be, for example, 20 to 30° C., and the humidity can be, for example, about 40 to 100%, specifically about 50 to 95%, and more specifically about 50 to 80%.

The carbon dioxide concentration can be, for example, about 300 to 5000 ppm, specifically about 500 to 3000 ppm, and more specifically about 1000 to 1500 ppm.

A fertilizer/liquid fertilizer can be selected appropriately according to the plant to be cultivated. In general, the fertilizer/liquid fertilizer contains nitrogen, phosphorus, and potassium.

The cultivation may performed in an open or (fully) closed plant factory.

In a case where the plant is a transgenic plant, a polypeptide or protein of interest can be extracted from a microbially infected part(s) of the plant, e.g., a microbially infected leaf or leaves, after about 3 to 7 days of cultivation.

<Fermented Plant Product Production Method>

The method of producing a fermented plant product in a plant according to the present disclosure includes:
  irradiating the plant with light in a wavelength range of 300 to 325 nm at a fluence of 4,000 to 50,000 µmol/m², while a fluence at wavelengths of 290 nm or less irradiated to the plant is less than 20% of that of the light in the wavelength range of 300 to 325 nm, or the plant is not irradiated with light at any wavelength of 290 nm or less;
  infecting the irradiated plant with a microorganism, and
  fermenting the infected plant to obtain the fermented plant product.

In other words, the fermented plant product production method according to the present disclosure includes a step of fermenting the plant treated by the plant treatment method according to the present disclosure.

The fermented plant product in the fermented plant product production method according to the present disclosure is a product by microbial fermentation of a plant raw material, preferably an edible plant raw material, and can be, for example, a brewed or fermented alcoholic beverage including fruit wine, a brewed or fermented vinegar, a brewed or fermented vegetable including a pickle, miso, soy sauce, a fermented tea, or the like.

Examples of fermented alcoholic beverages include wine (grape wine), cider (apple wine or fermented apple juice), etc.

Examples of brewed or fermented vinegars include grain vinegars such as a rice vinegar, a barley vinegar, a wheat vinegar, a malt vinegar, an adlay/job's tears vinegar, a soybean vinegar, a corn vinegar, and fruit vinegars such as an apple vinegar, a grape vinegar, a wine vinegar, a balsamic vinegar, and a persimmon vinegar.

Examples of miso include mugi (barely) miso (soybean paste fermented with fungi from barely), kome (rice) miso (soybean paste fermented with fungi from rice), mame (soybean) miso (soybean paste fermented with fungi from soybean), etc.

The plants that can be used in the present methods are plants that can be used as a raw material(s) for a fermented product to be produced, such as cereal grasses or grain plants (Poaceae), legumes, vegetable plants, and fruit plants.

Specific examples include rice, barley, wheat, corn, soybean, azuki bean, pea, *Brassica rapa* var. *glabra, Brassica. rapa* var. *toona* subvar. *hiroshimana, Brassica juncea* var. *integrifolia, Brassica campestris* var. *hakabura, Brassica rapa* var. *perviridis, Brassica campestris, Brassica rapa* var. *nipposinica, Raphanus sativus* var. *hortensis, Brassica rapa* var. *rapa, Cucumis sativus, Solanum melongena, Brassica oleracea* var. *capitata, Perilla frutescens* var. *crispa, Solanum tuberosum, Ipomoea batatas, Colocasia esculenta, Phyllostachys pubescens, Camellia sinensis*, and the like.

The irradiation step in the fermented plant product production method is as described above in the section "<Plant Treatment Method and Microorganism-infected Plant Production Method>."

The infection step in the fermented plant product production method is as described above in the section "<Plant Treatment Method and Microorganism-infected Plant Production Method>" except for the microorganism.

The microorganism in the fermented plant product production method can be a microorganism commonly used in the production of plant based fermented foods, including beverages, and can be a bacterium, a yeast, or a filamentous fungus.

Examples of bacteria include *Bacillus subtilis* subsp. *Natto*; plant *lactobacillus*, for example, lactic acid bacteria belonging to the genus *Lactobacillus* (e.g., *L. plantarum, L. brevis, L. casei,* and *L. paracasei*), the genus *Leuconostoc* (e.g., *L. mesenteroides*), the genus *Streptococcus*, the genus *Enterococcus* (e.g., *E. faecalis* and *E. faecium*), or the genus *Tetragenococcus* (e.g., *T. halophilus*); and acetic acid bacteria, for example, acetic acid bacteria belonging to the genus *Acetobacter* (e.g., *A. aceti*) or *Gluconacetobacter* (e.g., *G. xylinus*).

Specific examples of yeasts include those belonging to the genus *Saccharomyces* or *Zygosaccharomyces*, which can be more specifically, *S. cerevisiae, S. ellipsoideus, S. bayanus, S. pastorianus, Z. rouxii*, and the like.

Specific examples of filamentous fungi include those belonging to the genus *Aspergillus*, which can be more specifically, *A. oryzae, A. sojae, A. luchuensis, A. niger*, and the like.

The plant can be infected with a microorganism by bringing a microorganism suspension or a culture of microorganism, also called "starter", into contact with the plant.

The step of fermenting the plant infected with the microorganism (fermentation step) can be performed by a known method according to a fermented food to be produced.

According to the fermented plant product production method according to the present disclosure, the raw plant material can be infected with a higher number of microorganisms and therefore fermented in a shorter time due to accelerated fermentation, resulting in efficient production of the fermented plant product.

<Plant Treatment Apparatus>

The plant treatment apparatus according to the present disclosure includes:
  a plant holding unit configured to hold a plant;
  an ultraviolet irradiation unit configured to irradiate at least a portion of the plant held by the plant holding unit with ultraviolet light in a wavelength range of 300 to 325 nm, either without light at any wavelength of 290 nm or less or with light in wavelengths of 290 nm or less at a fluence that is less than 20% of a fluence of the light in the wavelength range of 300 to 325 nm; and
  a plant immersion unit including a tank, the tank being configured to hold a liquid containing a microorganism in a liquid holding space defined within a cavity of the tank, wherein the plant immersion unit is configured to allow the portion of the plant irradiated with the ultraviolet light to be located in the liquid holding space, or a liquid ejection unit configured to eject the liquid toward the portion of the plant irradiated with the ultraviolet light.

The plant treatment apparatus according to the present disclosure is suitable for performing the plant treatment method according to the present disclosure and the microorganism-infected plant production method according to the present disclosure, especially for performing the plant treatment method according to the present disclosure and the microorganism-infected plant production method according to the present disclosure in which the infecting is performed by an agroinfiltration method.

(Plant Holding Unit)

The plant holding unit has an discretionary structure that is capable of holding a plant and allows to place a portion, to be irradiated, of the plant held (the portion to be irradiated with ultraviolet light in a wavelength range of 300 to 325 nm), in an irradiation region of the ultraviolet irradiation unit, at least temporarily, for example, when the plant holding unit is in a predefined position ("ultraviolet irradiation position"). The portion to be irradiated may be the whole plant held, or one or more parts thereof.

The plant holding unit may hold a plant directly or indirectly via, e.g., a container, such as a container for nutrient solution cultivation, or more specifically a pot, which directly holds the plant and is held by the plant holding unit.

The plant holding unit can hold a plant in discretionary manner without particular limitation and may hold the plant by, for example, placing it thereon, accommodating it therein, or clamping or gripping or engaging it.

In embodiments of the plant treatment apparatus according to the present disclosure, including a plant immersion unit, the plant holding unit has a structure that is capable of holding a plant, preferably, in an upright position, i.e., with the aerial parts (or shoot system) upper and the underground parts lower, and/or in an inverted position. The plant holding unit may be capable of turning the held plant from the upright position to the inverted position or from the inverted position to the upright position and returning it to the upright position or the inverted position. This configuration facilitates the immersion of all or some of the aerial parts, for example, of the plant into the liquid containing the microorganism ("microorganism suspension") held in the tank of the plant immersion unit.

The plant holding unit may include a reflection member configured to surround the plant to be held and to reflect light from the ultraviolet irradiation unit toward the plant. This configuration makes it possible to irradiate an area(s) of the plant that is/are shaded from the light directly from the ultraviolet irradiation unit, thereby irradiating a larger area, which allows for efficient irradiation in terms of energy and/or time.

In certain embodiments, the plant holding unit includes a member to shield against light in the wavelength range of 300 to 325 nm. This configuration makes it possible to prevent or suppress an area(s), that is/are behind the shield member with respect to the light directly from the ultraviolet irradiation, of the plant held by the plant holding unit from irradiation with light from the ultraviolet irradiation unit.

(Ultraviolet Irradiation Unit)

The ultraviolet irradiation unit is configured to irradiate a plant held by the plant holding unit (hereinafter also referred to as "the subject plant to be irradiated") in a predefined position (ultraviolet irradiation position; first position) with ultraviolet light in a wavelength range of 300 to 325 nm (hereinafter also referred to as "specific ultraviolet light") at a fluence or photon flux density, while a fluence or photon flux density at wavelengths of 290 nm or less irradiated to the plant is less than 20%, preferably less than 10%, more preferably less than 5%, and more preferably less than 1% of the fluence or photon flux density of the light in the wavelength range of 300 to 325 nm, or the plant is not irradiated with light at any wavelength of 290 nm or less.

The ultraviolet irradiation unit includes a light source capable of emitting ultraviolet light in a wavelength range of 300 to 325 nm. The ultraviolet light in a wavelength range of 300 to 325 nm has the main peak wavelength preferably within 310±7 nm, more preferably within 310±5 nm, and more preferably 310±3 nm.

From the viewpoint of energy efficiency, it is preferable that the ultraviolet irradiation unit either does not irradiate light at any wavelength of 330 nm or more, or does irradiate light at wavelengths of 330 nm or more in a fluence or photon flux density that is less than 50%, preferably less than 30%, more preferably less than 20%, more preferably less than 10%, more preferably less than 5%, and more preferably less than 1%, of that of the light in the wavelength range of 300 to 325 nm.

Examples of light source of the ultraviolet irradiation unit include light emitting diodes (LEDs), laser diodes (LDs), as well as xenon lamps, fluorescent lamps, incandescent lamps, metal halide lamps, and high-pressure mercury lamps, which have a necessary optical filter. The optical filter can be an optical filter having a transmittance for light in the wavelength range of 300 to 325 nm higher than a transmittance for light at wavelengths of 290 nm or less, or an optical filter having a transmittance for light in the wavelength range of 300 to 325 nm higher than a transmittance for light at wavelengths of 290 nm or less and a transmittance for light at wavelengths of 330 nm or more.

As the aforementioned light source, a light emitting diode (LED) or a laser diode (LD) is particularly preferable. Use of an LED or LD can easily achieve irradiation with light in a wavelength range effective to reduce the plant's resistance to microbial infection while avoiding irradiation with light in a wavelength range that is not effective to reduce the plant's resistance to microbial infection or may have adverse effect on the plant. The use of an LED or LD is also preferred from the viewpoints of energy efficiency and economy due to energy intensiveness, low heat generation, low power consumption, and long life. In addition, the use of an LED or LD can facilitate control of photon flux density or fluence.

An LED or LD suitable as the light source is specifically an LED or LD having an emission spectrum with a peak wavelength of 310±7 nm and a full width at half maximum of 1 to 15 nm, more specifically 5 to 15 nm, and more specifically 5 to 10 nm, more specifically an LED or LD having an emission spectrum with a peak wavelength of 310±5 nm and a full width at half maximum of 1 to 15 nm, more specifically 5 to 15 nm, and more specifically 5 to 10 nm, and more specifically an LED or LD having an emission spectrum with a peak wavelength of 310±3 nm and a full width at half maximum of 1 to 15 nm, more specifically 5 to 15 nm, and more specifically 5 to 10 nm.

The LD or LED may be provided in the form of an array, matrix, or cluster.

The ultraviolet irradiation unit may irradiate the subject plant to be irradiated directly with specific ultraviolet light from any direction around the plant, e.g., in one or more directions from above and/or laterally to the plant.

The ultraviolet irradiation unit does not necessarily irradiate the entirety of the subject plant to be irradiated with the specific ultraviolet light. The ultraviolet irradiation unit, either by itself or together with the plant holding unit, more specifically the shield member that may be provided in the plant holding unit, can be configured to irradiate only a specific area of the subject plant to be irradiated with the specific ultraviolet light. The ultraviolet irradiation unit may be configured to emit the specific ultraviolet light as directional light.

The ultraviolet irradiation unit has an irradiation region where the photosynthetically active photon flux density is preferably 10 µmol/m$^2$/s or lower, more preferably 5 µmol/m$^2$/s or lower, more preferably 2 µmol/m$^2$/s or lower, and more preferably 1 µmol/m$^2$/s or lower, while irradiating ultraviolet light in a wavelength range of 300 to 325 nm. In certain embodiments, the ultraviolet irradiation unit is provided in an irradiation chamber that shields against photosynthetically active radiation from outside. As used herein, the expression "chamber that shields against photosynthetically active radiation from outside" means that, when lighting that can be provided in the chamber is turned off, the photosynthetically active photon flux density therein can be 10 µmol/m$^2$/s or lower, more specifically 5 µmol/m$^2$/s or lower, more specifically 2 µmol/m$^2$/s or lower, and more specifically 1 µmol/m$^2$/s or lower. The embodiments of the apparatus according to the present disclosure can hold a plant in a dark place, thereby substantially preventing or suppressing photosynthesis in the plant, allowing to cause efficiently reduced resistance of the plant to microbial infection when irradiated with the specific ultraviolet light from the ultraviolet irradiation unit.

The ultraviolet irradiation unit may include an optical system including one or more optical system components known in the art, such as a lens, a reflective mirror, an optical filter, a mask, and/or a diffusion plate. Additionally or alternatively, the ultraviolet irradiation unit may include a control unit to control the light source and/or the optical system.

The control unit may control a dimming of the light source and/or a timing of turning on and off the light source. The control unit may control which of continuous light, intermittent light, or a combination thereof is emitted by the ultraviolet irradiation unit. For the ultraviolet irradiation unit configured to emit intermittent light, the control unit may control a pulse width and/or a duty ratio of the intermittent light. Such a control unit can be, for example, a pulse width modulation circuit, or a pulse width modulation circuit and a timer, and may be constituted of, for example, a microcomputer, a relay, and/or a switching element.

The control unit may be configured to designate which of multiple light sources included in the ultraviolet irradiation unit to emit light according to information from a sensor. The multiple light sources can be in the form of an array, matrix, or cluster, for example.

In certain embodiments, the ultraviolet irradiation unit is configured to irradiate a specific portion of the plant held by the plant holding unit with specific ultraviolet light (preferably, specific ultraviolet light that is directional). The specific portion of the plant is detected or identified in advance by a sensor. The control unit may control the ultraviolet irradiation unit, according to information from the sensor, to emit the specific ultraviolet light toward the specific portion.

The sensor may form as a part of the ultraviolet irradiation unit, or may be provided in a sensor unit outside the ultraviolet irradiation unit.

(Plant Immersion Unit)

The plant immersion unit includes a tank capable of holding or storing a liquid in a liquid holding space defined within its cavity, and is configured to allow to place the UV-irradiated portion (the portion irradiated with the specific ultraviolet light by the ultraviolet irradiation unit) of the plant held by the plant holding unit, in the liquid holding space at a predefined position. The predefined position, which can also be called an immersion position, may be the position where the plant held by the plant holding unit is irradiated with the ultraviolet light by the ultraviolet irradiation unit (the ultraviolet irradiation position; first position), or may be a position different from the ultraviolet irradiation position (second position). In the former case, the plant is immersed into the microorganism suspension at the position where the plant was irradiated with the specific ultraviolet light.

When the liquid is held or stored in the liquid holding space, the UV-irradiated portion of the plant held by the plant holding unit in the immersion position is immersed into the liquid held in the liquid holding space.

The liquid is specifically a liquid containing a microorganism, i.e., a microorganism suspension.

The tank may have one or two openings, through which the plant held by the plant holding unit can be transported in and out of the cavity. The opening may, for example, be open at the top, or at a lateral side of the tank. The opening may have a rim along its periphery. The rim is configured to seal the cavity of the tank by closely contacting with a portion of a lid member as described below.

In certain embodiments, the plant immersion unit further includes a lid member configured to close the opening of the tank to seal its cavity. In the embodiments, when the plant is immersed into the microorganism suspension in the cavity, infiltration of the microorganism suspension into the plant tissues can be promoted by adjusting the pressure in the cavity. The pressure in the cavity may be adjusted by a pressure adjustment unit. In this embodiments, the tank may be configured to be able to function as a decompression chamber.

The lid member may include a sealing member or mechanism such as a sealant at the periphery of the opening or, if the opening has a peripheral rim, at the peripheral rim.

(Pressure Adjustment Unit)

The pressure adjustment unit includes a pressure reduction mechanism (also referred to as pressure reduction body) configured to be capable of reducing a pressure of the cavity of the tank when sealed with the lid member. The pressure reduction mechanism can be, for example, a vacuum pump. The pressure reduction mechanism is in fluid communication with the cavity of the tank via a valve.

The pressure reduction mechanism may be configured to reduce the pressure of the cavity of the tank to, for example, a pressure of 0.5 to 50 kPa, more specifically 0.5 to 30 kPa, more specifically 1 to 30 kPa, more specifically 1 to 20 kPa, more specifically 1 to 10 kPa, and more specifically 2 to 10 kPa.

The pressure adjustment unit may further include a member or mechanism, such as a pressure releasing valve, to restore the pressure in the cavity to ambient pressure, for example, near atmospheric pressure.

(Liquid Ejection Unit)

The liquid ejection unit is configured to be capable of ejecting a liquid to the UV-irradiated portion of the plant held by the plant holding unit at a predefined position. The predefined position, which can also be called an ejection position, may be the ultraviolet irradiation position (first position), or may be a position different from the ultraviolet irradiation position (second position). In the former case, the liquid is ejected toward the plant at the position where the plant was irradiated with the specific ultraviolet light. The liquid can be specifically a microorganism suspension.

The liquid ejection unit may have any structure capable of ejecting liquid to the plant held by the plant holding unit.

Ejection by the liquid ejection unit may be performed from any direction around the plant held by the plant holding unit, e.g., in one or more directions from above and/or laterally to the plant.

Ejection may be performed by using water pressure and/or air pressure. The ejection pattern or spray pattern may be in any shape, and may be, for example, straight, fan-shaped (flat), or full cone-shaped.

For example, the liquid ejection unit has one or more ejection ports to eject liquid towards the plant held by the plant holding unit. The ejection port is configured to be capable of ejecting liquid, or a mixture of liquid and gas. The ejection port is, for example, a single-fluid nozzle or a two-fluid nozzle.

The liquid ejection unit may eject a mist of liquid.

In certain embodiments, the liquid ejection unit is configured to be capable of ejecting a stream of liquid that is directed to a specific portion of the plant held by the plant holding unit. The specific portion of the plant is detected or identified in advance by a sensor. A control unit provided in the liquid ejection unit may control the direction of the ejection port, according to information from the sensor, to eject liquid toward the specific portion. The sensor may be provided in the ultraviolet irradiation unit, or may be provided in a sensor unit outside the ultraviolet irradiation unit.

(Sensor Unit)

In certain embodiments, the plant treatment apparatus according to the present disclosure includes a sensor unit that is configured to be capable of identifying a specific site of the plant held by the plant holding unit, according to information on color, shape and/or the like, and transmitting its positional information to the control unit provided in the ultraviolet irradiation unit. This can allow for efficient and reliable identification of a specific portion of the plant where the resistance to microbial infection is to be reduced, and efficient and reliable irradiation of the specific portion with the specific ultraviolet light by the plant treatment apparatus according to the present disclosure. The specific portion can include, for example, a specific organ(s), e.g., a leaf or leaves, a flower(s) and a (swollen) bud(s), or a root(s).

The sensor unit may be configured to be capable of transmitting the positional information to the control unit provided in the liquid ejection unit. This can allow for efficient and reliable ejection of a microorganism suspension by the plant treatment apparatus according to the present disclosure to the portion to be infected with a microorganism.

The sensor unit includes one or more sensors capable of distinguishing colors, shapes, and/or the like. The sensor can be, for example, a two-dimensional sensor, preferably a two-dimensional color sensor. Specific examples of sensors include, but are not limited to, monochrome or color image sensors, and can be CCD sensors, CMOS sensors, or the like. The sensor can be provided so that its sensing region covers the irradiation region of the ultraviolet irradiation unit.

(Photosynthetically Active Radiation Irradiation Unit)

The plant treatment apparatus according to the present disclosure may further include a photosynthetically active radiation irradiation unit.

The photosynthetically active radiation irradiation unit is configured to be capable of emitting photosynthetically active radiation to the plant held by the plant holding unit ("the subject plant to be irradiated") in a predefined position (photosynthetically active radiation irradiation position; third position).

The photosynthetically active radiation irradiation unit includes a light source capable of emitting light in a wavelength range of 400 to 700 nm. The light source used is not particularly limited as long as it can emit light suitable for growth of the subject plant to be irradiated, and can be any light source available in the art, including incandescent lamps, fluorescent lamps, white lamps, high intensity discharge (HID) lamps, such as high pressure sodium lamps, metal halide lamps, and high pressure mercury lamps, LEDs, such as white LEDs, cold cathode fluorescent lamps (CCFLs), organic EL lamps, or the like.

Among the above light sources, LEDs or LDs are particularly preferred in terms of energy efficiency and economy as well as ease of control and management. LDs or LEDs may be provided in the form of an array, matrix, or cluster.

The photosynthetically active radiation irradiation unit preferably irradiates the entirety of the subject plant to be irradiated with photosynthetically active radiation. The photosynthetically active photon flux density can be, for example, in a range of 50 to 600 $\mu mol/m^2/s$, and more specifically 100 to 500 $\mu mol/m^2/s$. The photosynthetically active radiation irradiation unit may irradiate the subject plant to be irradiated from any direction around the plant, but preferably from above the plant.

The photosynthetically active radiation irradiation unit may include a control unit that controls the conditions for photosynthetically active radiation. The conditions may include a light-dark cycle.

The photosynthetically active radiation irradiation unit(s) may be installed in a racking system (e.g., a multi-level racking system) for plant cultivation, which system configured to be capable of holding or storing plant holding units. The racking system may include a nutritious liquid supply system, which is installed in the racking system, as a nutritious liquid supply unit that supplies a nutritious liquid to the plants held by the plant holding units, which are held by the racking system.

(Plant Transportation Mechanism/Plant Transportation Body)

In some embodiments, the plant treatment apparatus according to the present disclosure includes a first transportation mechanism (also referred to as first transportation body) configurated to be capable of transporting the plant holding unit, at least from the ultraviolet irradiation unit to the plant immersion unit or to the liquid ejection unit. More specifically, the first transportation mechanism may be configured to be capable of transporting the plant holding unit, at least from the ultraviolet irradiation position (first position) in the ultraviolet irradiation unit to the immersion position in the plant immersion unit or to the ejection position in the liquid ejection unit (second position).

In certain embodiments including the plant immersion unit, the first transportation mechanism may include an inversion mechanism (also referred to as inversion body) that inverts the plant holding unit upside down between the ultraviolet irradiation position and the immersion position. This configuration facilitates, for example, the immersion of all or some of the aerial parts of the plant into the microorganism suspension stored in the tank of the plant immersion unit.

Preferably, the first transportation mechanism is configured to be capable of shielding, from photosynthetically active radiation, the plant holding unit (more specifically the plant held by the plant holding unit) on a transport path at least between the first position and the second position. For example, the transport path can be provided in a passage that is shielded against photosynthetically active radiation from the outside.

In some embodiments, the plant treatment apparatus according to the present disclosure, additionally or alternatively, includes a second transportation mechanism (also referred to as second transportation body) configured to be capable of transporting the plant holding unit, at least from the plant immersion unit or from the liquid ejection unit to the photosynthetically active radiation irradiation unit. More specifically, the second transportation mechanism may be configured to be capable of transporting the plant holding unit, at least from the second position to the third position.

Preferably, the second transportation mechanism is configured to be capable of shielding, from photosynthetically active radiation, the plant holding unit (more specifically the plant held by the plant holding unit) on a transport path at least between the second position and the third position. For example, the transport path can be provided in a passage that is shielded against photosynthetically active radiation from the outside.

The transportation mechanism can be provided with, for example, a conveyor stage(s), a transport or conveyor robot (s), or a robot arm(s).

The second transportation mechanism may be formed integrally with the first transportation mechanism.

A part(s) of the first and/or second transportation mechanism may constitute the plant holding unit.

The plant treatment apparatus according to the present disclosure will be described below with reference to FIGS. 1 and 2, which are exemplary schematic diagrams illustrating specific examples of embodiments of the plant treatment apparatus according to the present disclosure.

Embodiment 1

A plant treatment apparatus (100) according to the present disclosure, as illustrated in FIG. 1, includes a plant holding unit (110), an ultraviolet irradiation unit (120), a liquid ejection unit (130), and a control unit (140) that controls the ultraviolet irradiation unit (120) and the liquid ejection unit (130). The plant holding unit (110), the ultraviolet irradiation unit (120), and the liquid ejection unit (130) may be provided in a housing (180).

The plant holding unit (110) is capable of holding a plant (P). The plant treatment apparatus (100) may include a plurality of plant holding units (110).

The ultraviolet irradiation unit (120) includes a light source (122) capable of emitting ultraviolet light in a wavelength range of 300 to 325 nm, and a control unit (124) controlling the light source (122), and can emit the ultraviolet light in the wavelength range of 300 to 325 nm toward the plant (P). The light source (122) may be in the form of a light source array, such as an LD array or LED array.

The liquid ejection unit (130) is capable of ejecting liquid toward the plant (P) held by the plant holding unit (110). The liquid ejection unit (130) is controlled by the control unit (140) to eject liquid to the plant (P), which have been irradiated with ultraviolet light in the wavelength range of 300 to 325 nm by the ultraviolet irradiation unit (120). The liquid can be more specifically a microorganism suspension.

The housing (180) may be entirely composed of a light-shielding or substantially light-shielding material(s), or may be a dark chamber.

The plant treatment apparatus (100) may also be provided with a reflector (112), which can reflect ultraviolet light in the wavelength range of 300 to 325 nm. The reflector (112) may be provided in the plant holding unit (110), or may be arranged on at least a portion of the inner surface of the housing (180). The reflector (112) can reflect ultraviolet light in the wavelength range of 300 to 325 nm emitted from the ultraviolet irradiation unit (120) toward the plant (P) held by the plant holding unit (110).

Embodiment 2

A plant treatment apparatus (200) according to the present disclosure, as illustrated in FIG. 2, includes a plant holding unit (210), an ultraviolet irradiation unit (220), and a liquid immersion unit (240). The plant treatment apparatus (200) further includes a pressure adjustment unit (250) as an optional component.

The plant holding unit (210) is capable of holding a plant (P). The plant treatment apparatus (200) may include a plurality of plant holding units (210). The plant holding unit (210) may include a reflector that can reflect ultraviolet light in the wavelength range of 300 to 325 nm toward the held plant (P).

The plant holding unit (210) may be transported by a transportation mechanism from the irradiation region of the ultraviolet irradiation unit (220), more specifically from the ultraviolet irradiation position, to the liquid holding space defined in the cavity of a tank (242) of the liquid immersion unit (240), more specifically to the immersion position. The plant holding unit (210) may be inverted upside down while being transported or at the immersion position, to facilitate immersion.

The ultraviolet irradiation unit (220) includes a light source (222) capable of emitting ultraviolet light in a wavelength range of 300 to 325 nm, and a control unit (224) controlling the light source (222), and can emit the ultraviolet light in the wavelength range of 300 to 325 nm toward the plant (P). The light source (222) may be in the form of a light source array, such as an LD array or an LED array. The ultraviolet irradiation unit (220) may be provided in an irradiation chamber (280). In FIG. 2, the ultraviolet irradiation unit (220) is provided to irradiate the plant (P) from above. Additionally or alternatively, the ultraviolet irradiation unit (220) may be provided to irradiate the plant (P) from the lateral side and/or from below. Preferably, the irradiation chamber (280) can be shielded against photosynthetically active radiation from the outside.

The liquid immersion unit (240) includes the tank (242), which has the liquid holding space (244) defined in its cavity. The liquid immersion unit (240) further includes as optional structures, an opening (246) and a lid member (248), which closes the opening.

The liquid holding space (244) is capable of holding or storing liquid into which the plant (P) is immersed, more specifically a microorganism suspension. The opening (246) is provided for transporting the plant (P) held by the plant holding unit (210) in and out of the cavity of the tank (242). In FIG. 2, the opening (246) is open at the top of the tank. The opening may be open at a lateral side of the tank. The lid member (248) is capable of closing the opening (246) to seal the cavity.

The pressure adjustment unit (250) includes a vacuum pump (252) that is capable of reducing the pressure in the cavity of the tank 242 when sealed by the lid member (248), and a pressure releasing valve (254) that is capable of restoring the pressure in the cavity to a near atmospheric pressure. The vacuum pump (252) and the pressure releasing valve (254) are in fluid communication with the cavity of the tank (242) via a valve.

The plant (P) held by the plant holding unit (210) is transported into the cavity of the tank (242) through the opening (246). The plant (P) that is held by the plant holding unit (210) in the cavity in the immersion position after irradiated with ultraviolet light in the wavelength range of 300 to 325 nm by the ultraviolet irradiation unit (220), is immersed into the liquid held in the liquid holding space (244). After the plant is transported into the cavity of the tank (242), the lid member (248) closes the opening (246) to seal the cavity. After sealing, the cavity of the tank (242) is depressurized to a predefined pressure by the vacuum pump (252). After the passage of predefined period of time, the pressure releasing valve (254) is opened to restore the pressure in the cavity of the tank (242) to a near atmospheric pressure. In restoring, infiltration of the liquid into the plant (P) is accelerated. Thereafter, the plant (P) held by the plant holding unit (210) is transported through the opening (246) and out of the cavity of the tank (242).

EXAMPLES

Light Source

In the following examples, LEDs were used, which emit light having the peak wavelength (±full widths at half maximum) at 280 (±10) nm, 310 (±10) nm, and 340 (±10) nm (hereinafter also referred respectively to as "280 nm-LED light", "310 nm-LED light", and "340 nm-LED light"). FIG. 3 shows emission spectra of the LEDs used.

The 310 nm-LED light has predominantly wavelength components in the range of 300 to 325 nm, whereas the 280 nm-LED light and the 340 nm-LED light have almost no wavelength components in the range of 300 to 325 nm.

Example 1: Agroinfiltration Experiment 1

Materials and Methods

Cultivation of *Nicotiana benthamiana*

*Nicotiana benthamiana* was cultivated for approximately 4 weeks in soil ("YOSAKU," culture soil for fruit vegetables; JCAM AGRI. CO., LTD.). Cultivation conditions were as follows: a temperature of 24° C., 14 hours light, and white light illumination (at 100 μmol/m$^2$/s).

Preparation of *Agrobacterium* Suspension

*Agrobacterium* cells (strain LBA4404), into which an intron-containing firefly luciferase has been introduced, were grown in LB medium at 28° C. with shaking at 200 rpm, and the bacterial cells were collected at an OD600 of about 0.5 by centrifugation at 3,000 rpm for 15 minutes at room temperature. The precipitated bacterial cells were resuspended in an infiltration medium (10 mM $MgCl_2$, 10 mM MES, 150 μM acetosyringone, pH 5.7) to make an OD600 of 0.5 and allowed to stand in a dark place at room temperature for approximately 24 hours.

Ultraviolet LED Light Irradiation

About 4 week-old, potted *N. benthamiana* plants were used. As test sections, two treatment sections (LED light-irradiated and unirradiated sections) were provided in each of 1 to 3 leaves per plant. A half section of each leaf was covered with aluminum foil to shaded from light and used as LED light-unirradiated section (hereafter also simply referred to as "unirradiated section"); the remaining half section was used as LED light-irradiated section (hereafter also simply referred to as "irradiated section") (FIG. 4).

The leaves in which test sections were provided were irradiated with any one of the above-mentioned three LED lights at 2.5 μmol/m$^2$/s for 45 minutes (at a fluence of 6,750 μmol/m$^2$). Immediately after the irradiation, the aluminum foil strips were removed from the covered leaves.

*N. benthamiana* plants were then stored in a dark place for 24 hours.

Infection Treatment (Agroinfiltration) and Infection Confirmation

After 24 hours of dark place storage, the *Agrobacterium* suspension was applied with a needleless syringe to the irradiated and the unirradiated sections of the *N. benthamiana* leaves irradiated with the 310 nm-LED light or 340 nm-LED light. In each leaf, the same number (2 to 6) of applications were made in each of the treatment sections: the irradiated and unirradiated sections.

Immediately after the applications, the whole leaves was sprayed with a 0.2 mM D-luciferin solution.

After spraying, the leaves were left in a dark place at 22° C. for 24 hours.

After another 24 hours of dark place storage, the unirradiated and irradiated sections were imaged with a CCD color camera, and firefly luciferase luminescence was compared between the two treatment sections using image analysis. The luciferase luminescence in a leaf reflects the amount of *Agrobacterium* cells with introduced luciferase, infected into the leaf's cells.

Results

In the 280 nm-LED light irradiated section, significant wilting occurred with diminished water level and leaf thickness became thinner 24 hours after the irradiation (FIG. 5B). This trend is more significant in the leaves with no unirradiated section, that is, totally irradiated with the 280 nm-LED light. Because four week-old *N. benthamiana* plants have a low resistance to ultraviolet light, it is believed that the significant wilting occurred due to ultraviolet light stress caused by the 280 nm-LED light irradiation.

Because the 280 nm-LED light irradiated sections were not suitable for agroinfiltration, the 280 nm-LED light was not used in the subsequent experiments.

Figure 6:
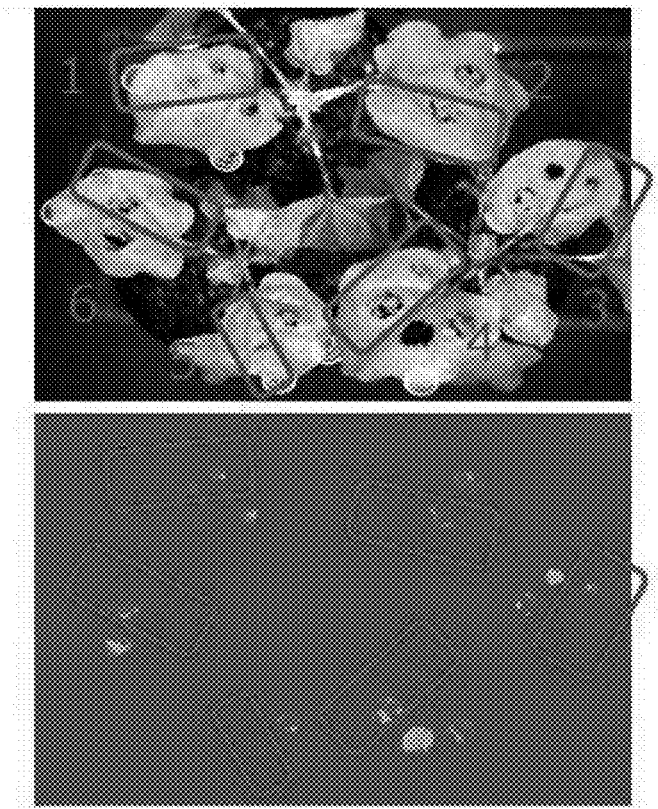
FIG. 6 shows luminescence images of the *Nicotiana benthamiana* leaves used in an experiment wherein irradiation was performed by 310 nm-LED light a fluence of 6750 μmol/m$^2$. Boxed are the unirradiated sections. Upper: a photograph of *Nicotiana benthamiana* leaves, superimposed with a firefly luciferase luminescence image to identify luminescent sites. Lower: a firefly luciferase luminescence image.
Figure 7:
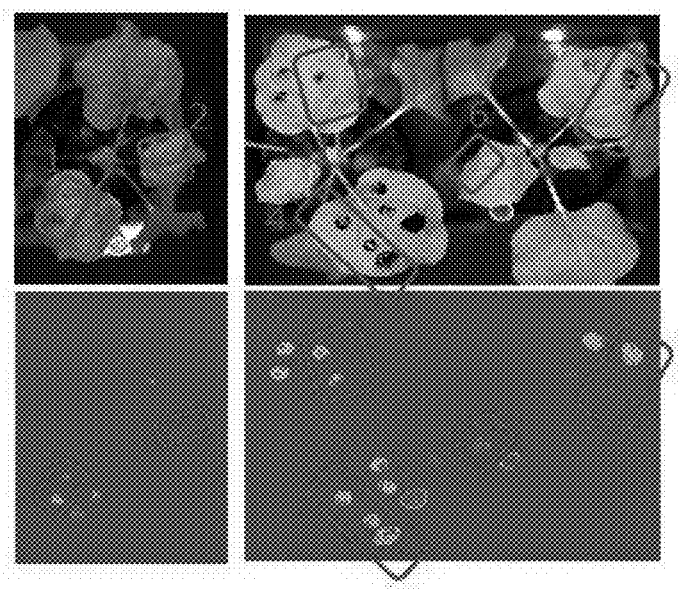
FIG. 7 shows luminescence images of the *Nicotiana benthamiana* leaves used in an experiment wherein irradiation was performed by 340 nm-LED light at a fluence of 6750 μmol/m$^2$. Boxed are the unirradiated sections. Upper: firefly luciferase luminescence images superimposed on photographs of *Nicotiana benthamiana*, identifying luminescent sites. Lower: a firefly luciferase luminescence image.

FIGS. 6 and 7 show luminescence images of the *N. benthamiana* leaves irradiated with the 310 nm-LED light and the 340 nm-LED light, respectively. The boxes indicate the unirradiated sections. Upper indicate photographs of *N. benthamiana* leaves, superimposed with firefly luciferase luminescence images. Lower indicate firefly luciferase luminescence images. In the upper photographs, black indicates high luminescence.

The 310 nm-LED light irradiated sections have markedly higher luminescence than the unirradiated sections (boxed in the figure) (FIG. 6). Thus, it is believed that the 310 nm-LED light irradiation increased *Agrobacterium* infection efficiency in plants, and it is deduced that this is due to reduced resistance of the plants to microbial infection.

On the other hand, in the leaves irradiated with the 340 nm-LED light, no difference in luminescence was observed between the irradiated and the unirradiated sections (FIG. 7). It is believed that this is because the 340 nm-LED light irradiation does not affect plant' resistance to microbial infection.

Figure 8:
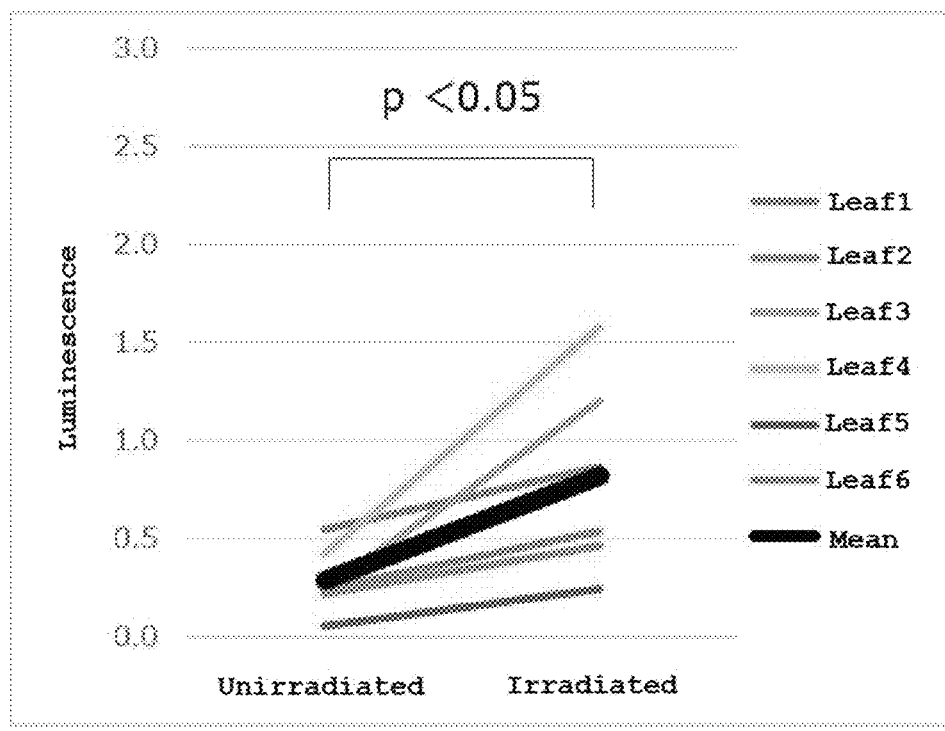
FIG. 8 shows luminescence of the unirradiated sections and the irradiated sections of the *Nicotiana benthamiana* leaves used in an experiment wherein irradiation was performed by 310 nm-LED light.
Figure 9:
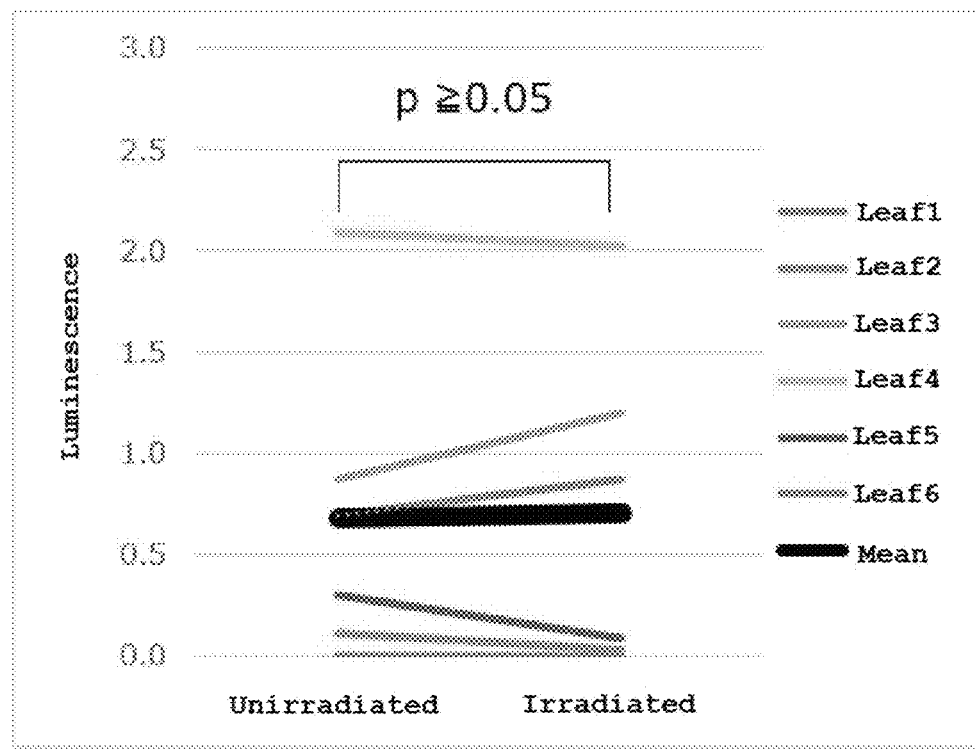
FIG. 9 shows luminescence of the unirradiated sections and the irradiated sections of the *Nicotiana benthamiana* leaves used in an experiment wherein irradiation was performed by 340 nm-LED light.
Figure 10:
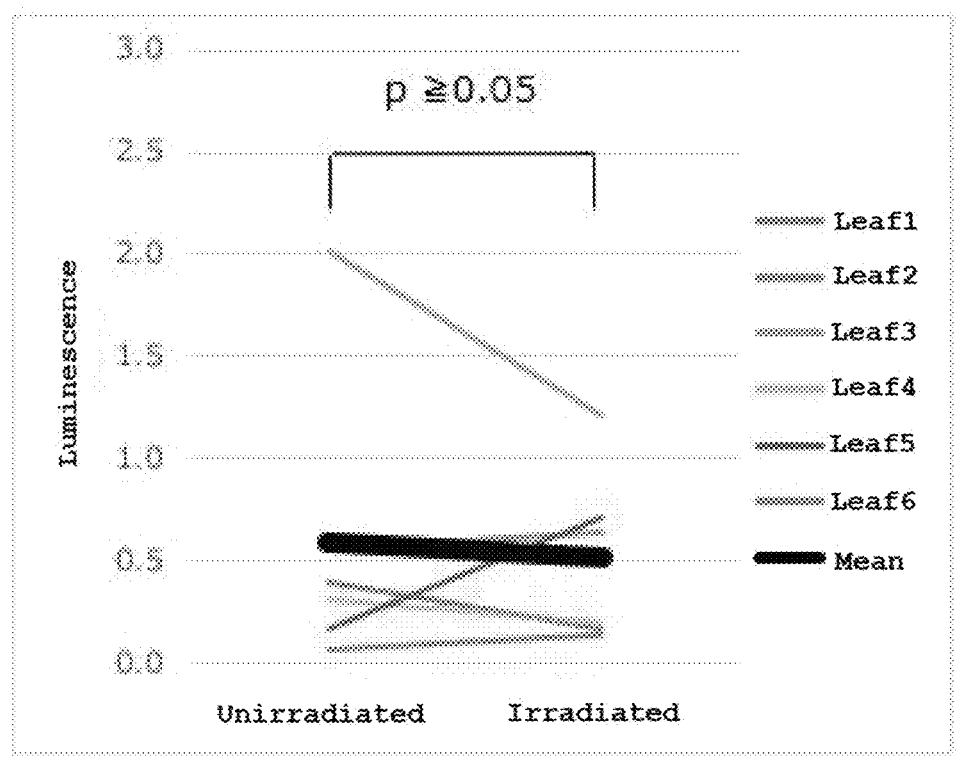
FIG. 10 shows luminescence of the unirradiated sections and the irradiated sections of the *Nicotiana benthamiana* leaves irradiated with 310 nm-LED light at a fluence of 675 µmol/m$^2$.
Figure 11:
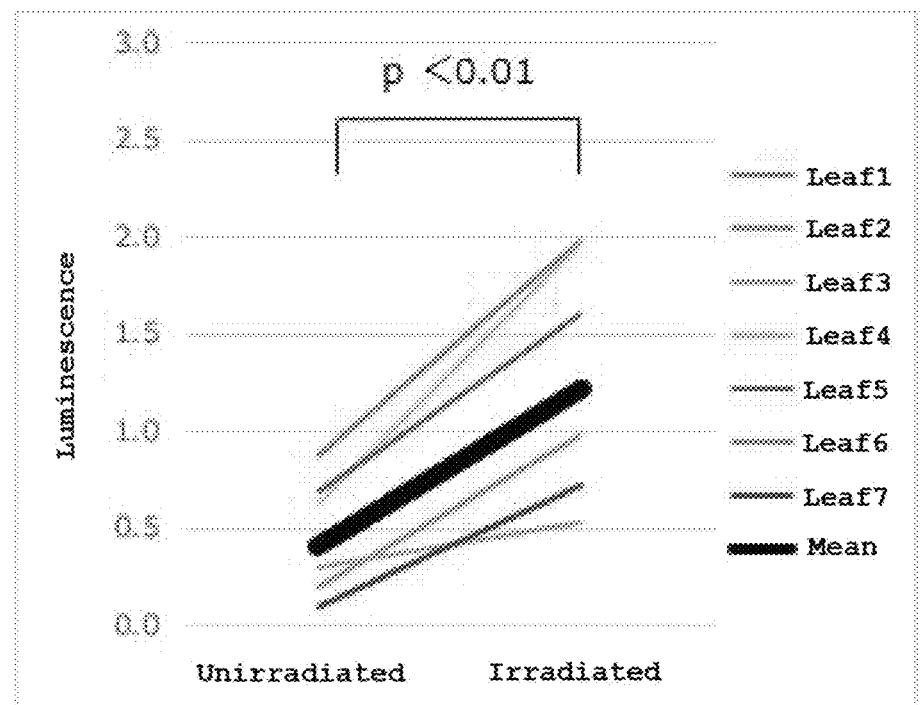
FIG. 11 shows luminescence of the unirradiated sections and the irradiated sections of the *Nicotiana benthamiana* leaves irradiated with 310 nm-LED light at a fluence of 13,500 µmol/m$^2$.

FIGS. 8 and 9 show luminescence in the test sections (unirradiated and irradiated sections) of each of the *N.*

*benthamiana* leaves irradiated with the 310 nm-LED light and the 340 nm-LED light, respectively. A two-tailed, paired t-test was used to compare luminescence in the unirradiated and the irradiated sections. As a result, the 310 nm-LED light irradiated sections had significantly increased luminescence compared to the unirradiated sections (FIG. 8; $p<0.05$). This indicates that more Agrobacteria cells can infect plant cells in the 310 nm-LED light irradiated sections than in the unirradiated sections.

On the other hand, no significant difference in luminescence was observed between the 340 nm-LED light irradiated and the unirradiated sections (FIG. 9; $p>0.05$). This indicates that the 340 nm-LED light irradiation does not affect *Agrobacterium* infection to plant cells.

From these results, it can be deduced that the 310 nm-LED light, but not the 340 nm-LED light, is capable of causing reduced resistance to microbial infection in plant cells.

Example 2: Agroinfiltration Experiment 2

Materials and Methods

The same as or similar to the experiment as in Example 1 was conducted, except that *N. benthamiana* leaves were irradiated with the 310 nm-LED light at 2.5 $\mu mol/m^2/s$ for 4.5, 90, 225, or 360 minutes (at a fluence of 675, 13,500, 33,750, or 54,000 $\mu mol/m^2$, respectively).

Results

Figure 12:
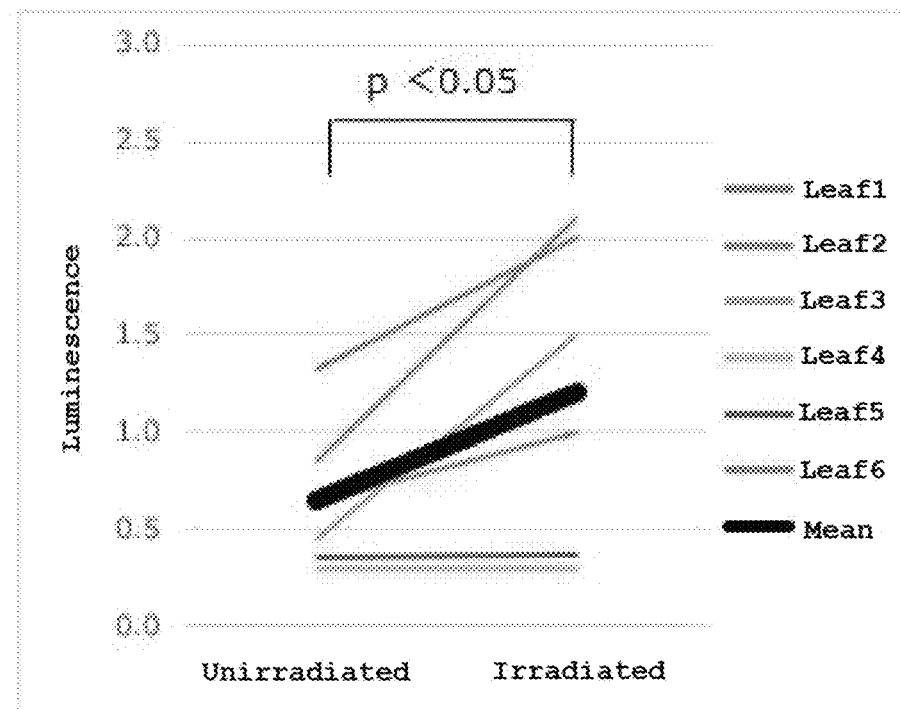
FIG. 12 shows luminescence of the unirradiated sections and the irradiated sections of the *Nicotiana benthamiana* leaves irradiated with 310 nm-LED light at a fluence of 33,750 µmol/m$^2$.
Figure 13:
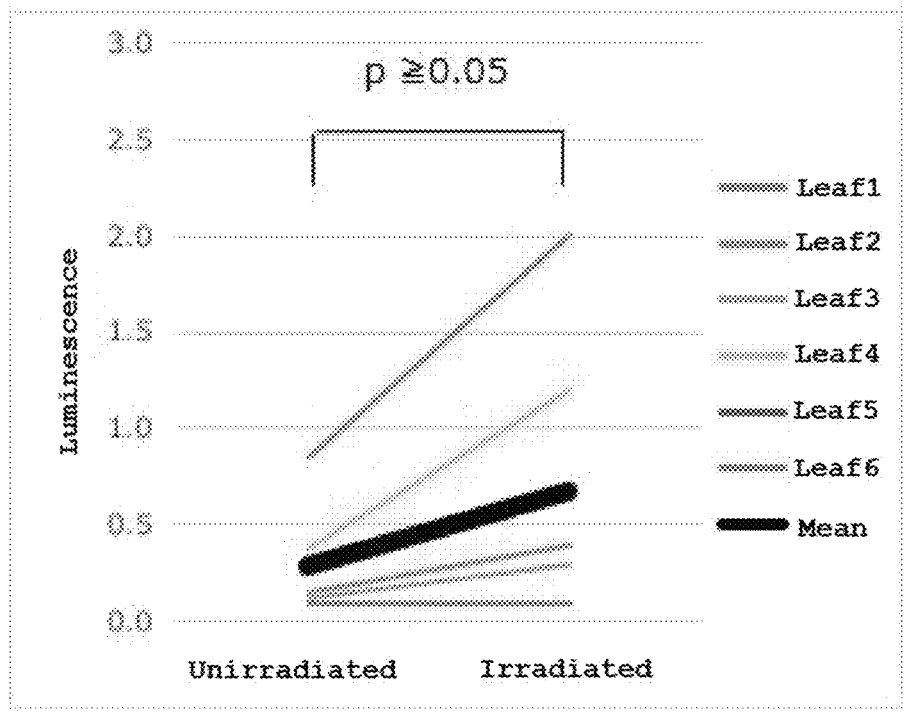
FIG. 13 shows luminescence of the unirradiated sections and the irradiated sections of the *Nicotiana benthamiana* leaves irradiated with 310 nm-LED light at a fluence of 54,000 µmol/m$^2$.

FIGS. 10 to 13 show luminescence in the test sections (unirradiated and irradiated sections) of each of the *N. benthamiana* leaves irradiated with the 310 nm-LED light at fluences of 675, 13,500, 33,750, and 54,000 $\mu mol/m^2$, respectively. A two-tailed, paired t-test was used to compare luminescence in the unirradiated and the irradiated sections. As a result, the sections irradiated at fluences of 13,500 and 33,750 $\mu mol/m^2$ had significantly increased luminescence compared to the unirradiated sections (FIG. 11, $p<0.01$; FIG. 12, $p<0.05$). On the other hand, no significant difference in luminescence was observed between the sections irradiated at a fluence of 675 $\mu mol/m^2$ and the unirradiated sections (FIG. 10; $p>0.05$). The sections irradiated at a fluence of 54,000 $\mu mol/m^2$ had a tendency to increase luminescence compared to the non-irradiation sections, while showing a tendency of wilting.

Figure 14:
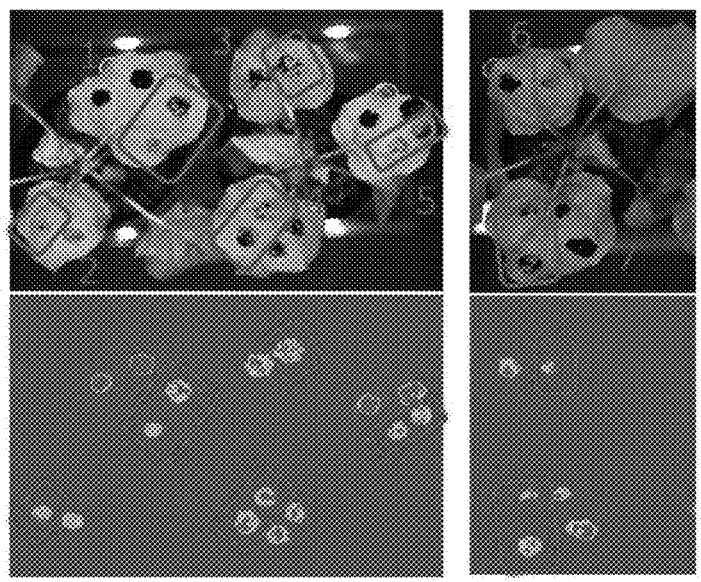
FIG. 14 shows luminescence images of the *Nicotiana benthamiana* leaves used in an experiment wherein irradiation was performed by 310 nm-LED light at a fluence of 13,500 µmol/m$^2$. Boxed are the unirradiated sections. Upper: a photograph of *Nicotiana benthamiana* leaves, superimposed with a firefly luciferase luminescence image to identify luminescent sites. Lower: firefly luciferase luminescence.

FIG. 14 shows luminescence images of the *N. benthamiana* leaves irradiated with the 310 nm-LED light at a fluence of 13,500 $\mu mol/m^2$. Boxed are the unirradiated sections. Upper indicate photographs of *N. benthamiana* leaves, superimposed with firefly luciferase luminescence images. Lower indicate firefly luciferase luminescence images. In the upper photographs, black indicates high luminescence. As can be seen from the figure, the 310 nm-LED light irradiated sections have markedly higher luminescence than the unirradiated sections (boxed in the figure).

From these results together with the results of Example 1, it can be deduced that the 310 nm-LED light irradiation at a fluence of about 1,000 to 4,000 $\mu mol/m^2$ or more can cause reduced resistance of plant cells to microbial infection, but the irradiation at a fluence of 54,000 $\mu mol/m^2$ or more may damage the plant cells.

Example 3: Agroinfiltration Experiment 3

Material and Methods

The same as or similar to the experiment as in Example 1 was conducted, except that the plants were irradiated with the 310 nm-LED light only and were not stored in a dark place.

Results

Figure 15:
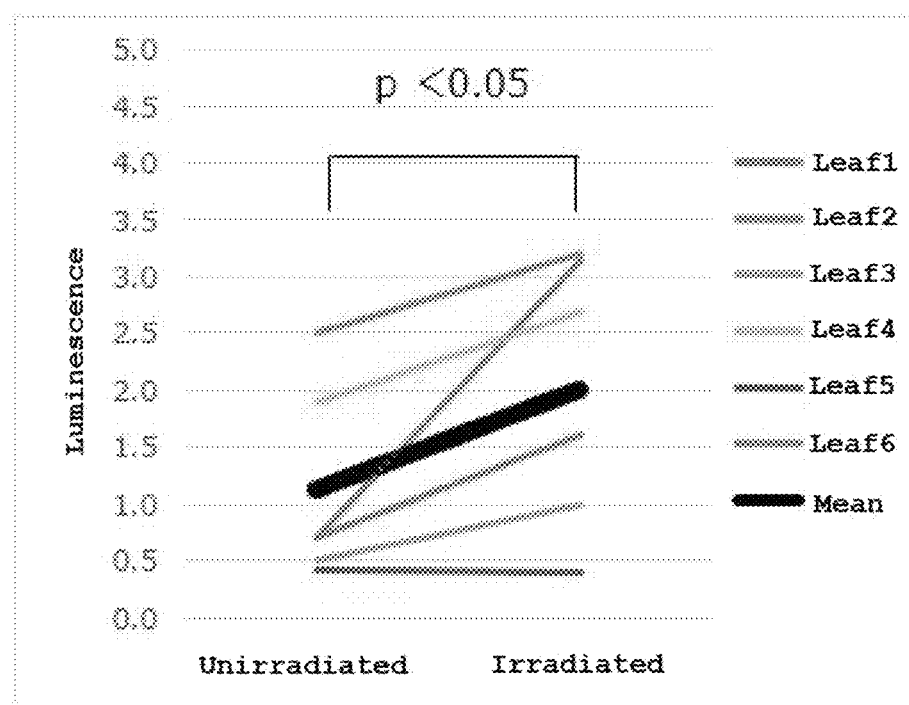
FIG. 15 shows luminescence of the unirradiated sections and the irradiated sections of the *Nicotiana benthamiana* leaves infiltrated with *Agrobacterium* using a needleless syringe immediately after irradiation with 310 nm-LED light at a fluence of 6,750 µmol/m$^2$.

FIG. 15 shows luminescence in the test sections (unirradiated and irradiated sections) of each of the *N. benthamiana* leaves irradiated with the 310 nm-LED light at fluences of 6,750 $\mu mol/m^2$. The 310 nm-LED light irradiated sections had significantly increased luminescence than the unirradiated sections (two-tailed, paired t-test, $p<0.05$). From these results, it can be deduced that plants irradiated with the 310 nm-LED light have significantly reduced resistance to microbial infection immediately after the irradiation.

Example 4: Floral Inoculation Experiment

Materials and Methods

Flower buds of *Arabidopsis thaliana* plants were irradiated with the 310 nm-LED light at a fluence of 6,750 $\mu mol/m^2$ (=2.5 $\mu mol/m^2/s \times 45$ min), and then inoculated with a suspension of *Agrobacterium* cells with introduced kanamycin-resistant gene in a culture medium, using a micropipette (floral inoculation), according to the method of M. Narusaka et al. (*Plant Biotechnology* 27, 349-351, 2010).

The *A. thaliana* plants were grown until the flower buds flowered to produce seeds, according to the conventional method, and then dried seeds were harvested.

As controls, dried seeds were harvested from the flower buds of other *A. thaliana* plants, which had been subjected to the same floral inoculation as described above without the 310 nm-LED light irradiation.

Two hundred sixty-four (264) dried seeds from the flower buds irradiated with the 310 nm-LED light and 1,000 dried seeds from the unirradiated flower buds were sown on an agar medium (MS medium) containing kanamycin for kanamycin selection.

Results

None of the seeds from the unirradiated buds grew on the kanamycin-containing agar medium. This suggests that genetic recombination did not occur in the flower buds subjected to floral inoculation without 310 nm-LED light irradiation.

On the other hand, two of the 264 seeds from the flower buds subjected to the floral inoculation after the 310 nm-LED light irradiation grew on the kanamycin-containing agar medium. This suggests that genetic recombination efficiency was increased in the flower buds subjected to the floral inoculation after the 310 nm-LED light irradiation.

From these results, it can be seen that the 310 nm-LED light irradiation can increase the efficiency of genetic recombination following floral inoculation. Considering the results of Examples 1 to 3, it can be deduced that the increased genetic recombination efficiency would result from the reduced resistance of the flower buds to microbial infection, induced by the 310 nm-LED light irradiation.

Example 5: Gene Expression Analysis of *A. thaliana* Plants Irradiated with the 310 nm-LED Light A gene expression analysis was performed on *A. thaliana* plants immediately after irradiated with the 310 nm-LED light at a fluence of 6,750 $\mu mol/m^2$ (=2.5 $\mu mol/m^2/s \times 45$ min).

Results

In the *A. thaliana* plants irradiated with the 310 nm-LED light, transcription factors (WRKY60, MYB28, MYB29, and MYB45), involving plant defense against bacteria and filamentous fungi, and salicylic acid response-related genes (UGT1 and PARN) were significantly down-regulated.

In addition, downregulation was observed in also genes (GAD1 and ALDH2B7) associated with biosynthesis of GABA, which is known to inhibit gene transfer into plants by *Agrobacterium*.

Therefore, it can be deduced that the 310 nm-LED light weakens the defense mechanism of plant cells against bacteria and filamentous fungi (in other words, reduces the resistance to microbial infection), and also suppresses the GABA biosynthesis in the cells, thereby promoting microbial infection into plant cells.

The methods according to the present disclosure in some embodiments can be used to produce a recombinant protein that may be used as a material for biopharmaceuticals (such as interferons, immunogens for vaccines, antibodies, antigens, and growth factors), industrial enzymes (such as cellulases, proteases, and amylases), foods and diets (such as protein supplements and nutrients) and others.

The methods according to the present disclosure in some embodiments can be used to produce a transgenic plant. The methods according to the present disclosure are particularly suitable for use in a plant into which a gene is not efficiently transferred due to its high disease resistance or low seed yield at a time.

The methods according to the present disclosure in some embodiments can be used to efficiently produce a fermented plant product.

The methods according to the present disclosure in some embodiments can be used to produce a plant that can grow under various environmental stress conditions.

What is claimed is:

1. A method of treating a plant, the method comprising:
   irradiating the plant with light in a wavelength range of 300 nm to 325 nm at a fluence of 4,000 μmol/m² to 50,000 μmol/m², while a fluence of light in a wavelength range of 290 nm or less irradiated to the plant is less than 20% of the fluence of the light in the wavelength range of 300 nm to 325 nm, or the plant is not irradiated with light at any wavelength of 290 nm or less; and then
   infecting the plant with a microorganism.

2. The method according to claim 1, wherein the microorganism carries a foreign gene of interest.

3. The method according to claim 1, wherein the irradiating is performed in a dark place.

4. The method according to claim 1, wherein the method further comprises placing the plant obtained in the infecting in a dark place for a period of 6 hours to 48 hours.

5. The method according to claim 1, wherein the method further comprises growing the plant obtained in the infecting.

6. The method according to claim 1, wherein in the irradiating, the light in the wavelength range of 300 nm to 325 nm is irradiated to the plant at a photon flux density of 0.05 μmol/m² to 300 μmol/m²/s.

7. The method according to claim 1, wherein in the irradiating, the plant is not irradiated with light at any wavelength of 330 nm or more, or a fluence of light in a wavelength range of 330 nm or more irradiated to the plant is less than 30% of the fluence of the light in the wavelength range of 300 nm to 325 nm.

8. The method according to claim 1, wherein the infecting is performed by immersing the plant into a liquid containing the microorganism, or by spraying the liquid containing the microorganism onto the plant or injecting the liquid containing the microorganism into the plant.

9. The method according to claim 1, wherein the infecting is performed by an agroinfiltration method or a plant virus vector method.

10. The method according to claim 1, wherein the light in the wavelength range of 300 nm to 325 nm has a wavelength spectrum with a peak wavelength of 310±5 nm and a full width at half maximum in a range from 5 nm to 15 nm.

11. The method according to claim 1, wherein the infecting is performed in a greenhouse.

12. The method according to claim 1, wherein the microorganism is a microbial pesticide.

13. A method of producing a plant infected with a microorganism, the method comprising:
   irradiating a plant with light in a wavelength range of 300 nm to 325 nm at a fluence of 4,000 μmol/m² to 50,000 μmol/m², while a fluence of light in a wavelength range of 290 nm or less irradiated to the plant is less than 20% of the fluence of the light in the wavelength range of 300 nm to 325 nm, or the plant is not irradiated with light at any wavelength of 290 nm or less; and then
   infecting the plant with the microorganism.

14. A method of producing a fermented plant product, the method comprising:
   the irradiating and the infecting according to claim 13; and then
   fermenting the plant to obtain the fermented plant product.

* * * * *